United States Patent [19]
Miyake et al.

[11] Patent Number: 5,389,633
[45] Date of Patent: Feb. 14, 1995

[54] TRIAZOLOPYRIDAZINE COMPOUNDS, THEIR PRODUCTION AND USE

[75] Inventors: Akio Miyake, Hirakata; Yasuhiko Kawano, Suita; Yasuko Ashida, Takatsuki, all of Japan

[73] Assignee: Takeda Chemical Industries, Ltd., Osaka, Japan

[21] Appl. No.: 32,296

[22] Filed: Mar. 17, 1993

[30] Foreign Application Priority Data

Mar. 18, 1992 [JP] Japan .................. 4-061780
Aug. 18, 1992 [JP] Japan .................. 4-218904
Feb. 1, 1993 [JP] Japan .................. 5-014560

[51] Int. Cl.⁶ .................. A61K 31/535; A61K 31/50; C07D 487/04; C07D 471/14
[52] U.S. Cl. .................. 514/233.2; 514/248; 544/234; 544/236; 558/12; 560/150; 560/226; 564/95; 564/98
[58] Field of Search .................. 514/248, 233.2; 544/236, 115, 118

[56] References Cited

U.S. PATENT DOCUMENTS

| | | | |
|---|---|---|---|
| 5,145,850 | 9/1992 | Miyake et al. | 544/236 |
| 5,155,108 | 10/1992 | Miyake et al. | 544/236 |
| 5,202,324 | 4/1993 | Miyake et al. | 544/236 |

FOREIGN PATENT DOCUMENTS

| | | |
|---|---|---|
| 0381132 | 8/1990 | European Pat. Off. . |
| 0440119 | 8/1991 | European Pat. Off. . |
| 0444549 | 9/1991 | European Pat. Off. . |

*Primary Examiner*—Emily Bernhardt
*Attorney, Agent, or Firm*—Foley & Lardner

[57] ABSTRACT

Novel compound represented by the formula:

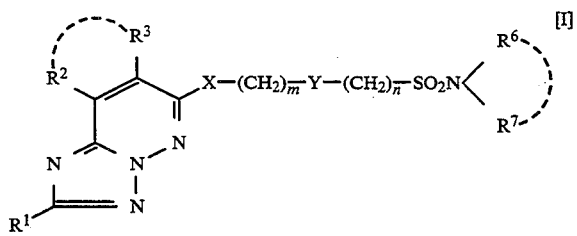

wherein $R^1$ stands for H, an optionally substituted lower alkyl group or a halogen; $R^2$ and $R^3$ respectively stands for a hydrogen or an optionally substituted lower alkyl group, or $R^2$ and $R^3$ may, taken together with the adjacent —C=C— group, form a 5- to 7-membered ring; X stands for O, SO or $SO_2$; Y stands for a group of the formula:

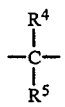

($R^4$ and $R^5$ respectively stand for H or an optionally substituted lower alkyl group) or a divalent group derived from an optionally substituted 3- to 7-membered homocyclic or heterocyclic ring; $R^6$ and $R^7$ each stands for H, an optionally substituted lower alkyl group, an optionally substituted cycloalkyl group or an optionally substituted aryl group, or $R^6$ and $R^7$ may, taken together with the adjacent N, form an optionally substituted N-containing heterocyclic group; m stands for 0 to 4; n stands for 0 to 4, or a salt thereof, which has excellent anti-PAF activities anti-$LTC_4$ activities and anti-ET-1 activities, and is of value as an antiasthmatic agent, and their production, intermediates and pharmasceutical compositions.

23 Claims, No Drawings

TRIAZOLOPYRIDAZINE COMPOUNDS, THEIR PRODUCTION AND USE

The present invention relates to triazolopyridazine derivatives and their salts, their production, intermediates, and pharmaceutical compositions. The triazolopyridazine derivative and its salt of the present invention have antiallergic, antiinflammatory and anti-PAF (platelet activating factor) activities and, by virtue of their inhibitory action on bronchospasm and bronchoconstriction, can be used as effective antiasthmatic agents.

While a large number of triazolopyridazine compounds are synthesized of late for use as drugs effective against a variety of diseases, U.S. Pat. No. 3,915,968 discloses a compound of the formula:

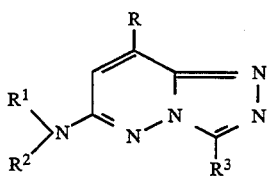

wherein R and $R^3$ independently stand for a hydrogen atom or a lower alkyl group (at least one of R and $R^3$ is lower alkyl); $R^1$ and $R^2$, taken together with the nitrogen atom, stand for a heterocyclic group selected from among pyrrolidine, piperidine, piperazine and morpholine, or a salt thereof;

U.S. Pat. No. 4,136,182 discloses a compound of the formula:

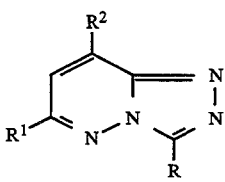

wherein R stand for hydrogen, phenyl or lower alkyl-carbonylamino; $R^1$ stands for morpholino or piperidino; $R^2$ means hydrogen or lower alkyl; provided, however, that at least one of R and $R^2$ is a species other than hydrogen and further that when R is phenyl, $R^1$ stands for morpholino and $R^2$ stands for lower alkyl, or a salt thereof; EP-A-0 248 413 describes a compound of the formula:

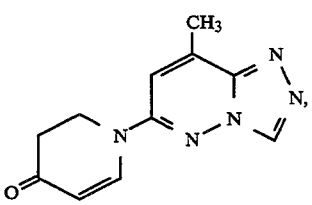

or a salt thereof, all noting to the effect that the respective compounds are of use as bronchodilators effective for relief of bronchospasms.

Although a wide variety of antiasthmatic drugs are now commercially available, none are satisfactory as to action sustainability, safety and other properties. It is therefore desired that a new compound be developed which exhibits more antiallergic, anti-inflammatory and anti-PAF activities and which is excellent in action sustainability, safety and other properties for an antiasthmatic drug.

The present inventors investigated the chemical modefication of [1,2,4]triazolo[1,5-b]pyridazine compounds at the 6 position, and found that a new series of [1,2,4]triazolo[1,5-b]pyridazine compounds structurally different from the above-mentioned known compounds unexpectedly exhibited highly antiallergic, anti-inflammatory and anti-PAF activities and excellent action substainability and safety. They further found that these compounds inhibit bronchospasm and bronchoconstriction and, therefore, could be utilized as effective antiasthmatic agents. Based on these findings, the present invention has been accomplished.

Thus, the present invention provides
(1) a compound of the general formula:

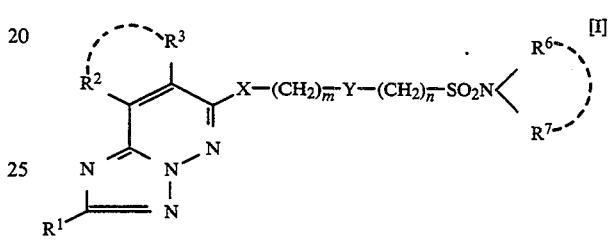

wherein $R^1$ stands for a hydrogen atom, an optionally substituted lower alkyl group or a halogen atom; $R^2$ and $R^3$ each stands for a hydrogen atom or an optionally substituted lower alkyl group, or $R^2$ and $R^3$ may, taken together with the adjacent —C=C— group, form a 5- to 7-membered ring; X stands for an oxygen atom or $S(O)_p$ (p stands for a whole number of 0 to 2); Y stands for a group of the formula:

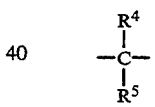

($R^4$ and $R^5$ each is a hydrogen atom or an optionally substituted lower alkyl group) or a divalent group derived from an optionally substituted 3- to 7-membered homocyclic or heterocyclic ring; $R^6$ and $R^7$ each stands for a hydrogen atom, an optionally substituted lower alkyl group, an optionally substituted cycloalkyl group or an optionally substituted aryl group, or $R^6$ and $R^7$ may, taken together with the adjacent nitrogen atom, form an optionally substituted nitrogen-containing heterocyclic group; m stands for a whole number of 0 to 4; n stands for a whole number of 0 to 4, or a salt thereof, (2) a process for producing a compound described above in (1) which comprises reacting a compound of the general formula:

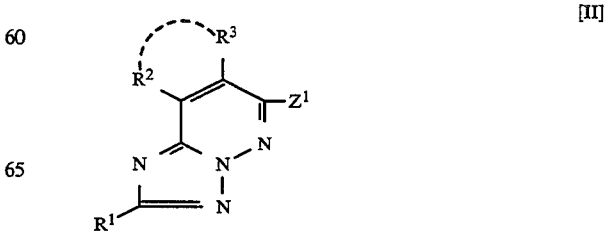

wherein $Z^1$ means a reactive group; $R^1$, $R^2$ and $R^3$ are as defined above, or a salt thereof with a compound of the general formula:

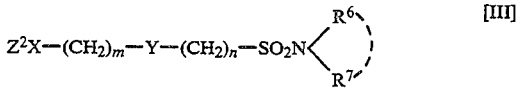

[III]

wherein $Z^2$ means a group which leaves on reacting with $Z^1$; X, Y, $R^6$, $R^7$, m and n are as defined above, or a salt thereof, (3) a process for producing a compound described above in (1) which comprises reacting a compound of the general formula:

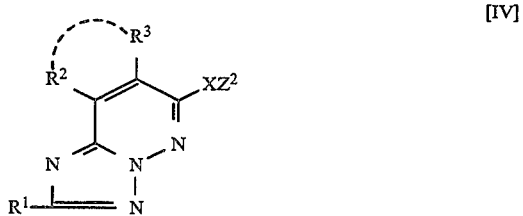

[IV]

wherein $Z^2$, $R^1$, $R^2$, $R^3$ and X are as defined above, or a salt thereof with a compound of the general formula:

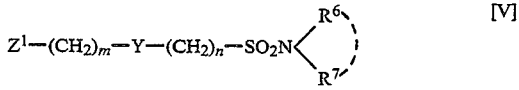

[V]

wherein $Z^1$, Y, $R^6$, $R^7$, m and n are as defined above, or a salt thereof, (4) a process for producing a compound described above in (1) which comprises reacting a compound of the general formula:

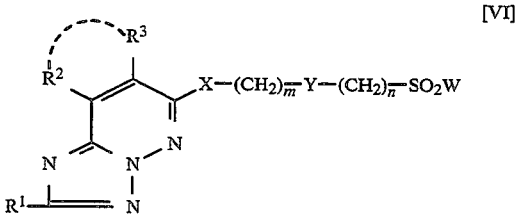

[VI]

wherein W means a leaving group; $R^1$, $R^2$, $R^3$, X, Y, m and n are as defined above, or a salt thereof with a compound of the general formula:

[VII]

wherein $R^6$ and $R^7$ are as defined above, or a salt thereof, (5) an antiasthmatic composition characterized by containing the compound [I] or a salt thereof, (6) an anti-PAF composition characterized by containing the compound [I] or a salt thereof, (7) the compound [VI] or a salt thereof.

It should be understood that where the compound [I] or a salt thereof contains asymmetric carbon within its structure, it may occur as optically active isomers as well as racemic mixtures and that these isomers and mixtures also fall within the scope of the invention.

As used throughout this specification, the term 'lower alkyl' means inter alia a straight-chain or branched $C_{1-6}$ alkyl group. The $C_{1-6}$ alkyl group includes methyl, ethyl, n-propyl, i-propyl, n-butyl, i-butyl, tert-butyl, n-pentyl, n-hexyl and so on.

The term 'cycloalkyl' means inter alia a $C_{3-6}$ cycloalkyl group. The $C_{3-6}$ cycloalkyl group includes cyclopropyl, cyclobutyl, cyclopentyl and cyclohexyl.

The term 'aryl' means inter alia a $C_{6-14}$ aryl group. The $C_{6-14}$ aryl group includes phenyl, naphthyl and so on.

Substituent group(s) by which said 'lower alkyl' and 'cycloalkyl' may optionally be substituted, may range from 1 to 4 in number and are selected from among hydroxy, amino, carboxyl, nitro, mono- or di-lower alkylamino (e.g. mono- or di-$C_{1-6}$ alkylamino groups such as methylamino, ethylamino, propylamino, dimethylamino, diethylamino, etc.), lower alkoxy (e.g. $C_{1-6}$ alkoxy groups such as methoxy, ethoxy, propoxy, hexyloxy, etc.), lower alkylcarbonyloxy (e.g. $C_{1-6}$ alkylcarbonyloxy groups such as acetoxy, ethylcarbonyloxy, etc.), halogen (e.g. fluorine, chlorine, bromine and iodine) and so on.

Substituent group(s) by which said 'aryl' group may optionally be substituted, may range from 1 to 5 in number and are selected from among optionally substituted lower alkyl, optionally substituted amino, acetamido, hydroxy, carboxyl, nitro, lower alkoxy (e.g. $C_{1-6}$ alkoxy groups such as methoxy, ethoxy, propoxy, etc.), lower alkylcarbonyloxy (e.g. $C_{1-6}$ alkylcarbonyloxy groups such as acetoxy, ethylcarbonyloxy, etc.), halogen atoms (e.g. fluorine, chlorine, bromine and iodine) and so on. In this connection, substituent group(s) by which the lower alkyl (e.g. $C_{1-6}$ alkyl group such as methyl, ethyl, n-propyl, etc.) mentioned just above may be substituted, may range from 1 to 4 in number and are selected from among hydroxy, amino, mono- or di-lower alkylamino (e.g. mono- or di-$C_{1-6}$ alkylamino groups such as methylamino, ethylamino, propylamino, dimethylamino, diethylamino, etc.), lower alkoxy (e.g. $C_{1-6}$ alkoxy groups such as methoxy, ethoxy, propoxy, hexyloxy, etc.), halogen (e.g. fluorine, chlorine, bromine and iodine) and so on. Substituent group(s) by which the amino group mentioned above may be substituted, may range from 1 to 2 in number and are selected from among $C_{1-6}$ alkyl (e.g. methyl, ethyl, propyl, etc.), 5- to 7-membered cyclic amino (e.g. pyrrolidino, morpholino, piperidino, piperazino, etc.) and so on.

The term 'halogen' means fluorine, chlorine, bromine or iodine, for instance.

The '5- to 7-membered ring formed in combination with the adjacent —C≡C— group' means a 5- to 7-membered ring such as, for example, rings which may contain 1 to 4 hetero-atoms selected from among nitrogen, oxygen, sulfur, etc. in addition to carbon atoms. Thus, in particular, 5- to 7-membered hydrocarbon rings, e.g. $C_{5-7}$ cycloalkenes such as cyclopentene, cyclohexene, cycloheptene, etc., benzene and so on and a 5- or 6-membered nitrogen-containing heterocyclic groups consisting of carbon and nitrogen atoms, such as pyrrole, pyridine, piperidine, etc., can be mentioned as the common species.

The term '3- to 7-membered homocyclic ring' means a 3- to 7-membered homocyclic ring consisting exclusively of carbon atoms, for instance. Thus, for example, $C_{3-7}$ cycloalkanes such as cyclopropane, cyclobutane, cyclopentane, cyclohexane, cycloheptane, etc., $C_{3-7}$ cycloalkenes such as cyclopropene, cyclobutene, cyclopentene, cyclohexene, cycloheptene, etc. and benzene can be mentioned as the common species.

The divalent group derived from said "3- to 7-membered homocyclic ring" is a group resulting from either elimination of two hydrogen atoms from a single carbon atom in the 3- to 7-membered homocyclic ring or elimination of one hydrogen atom from each of two different carbon atoms. To be specific, the following groups can be included by way of example.

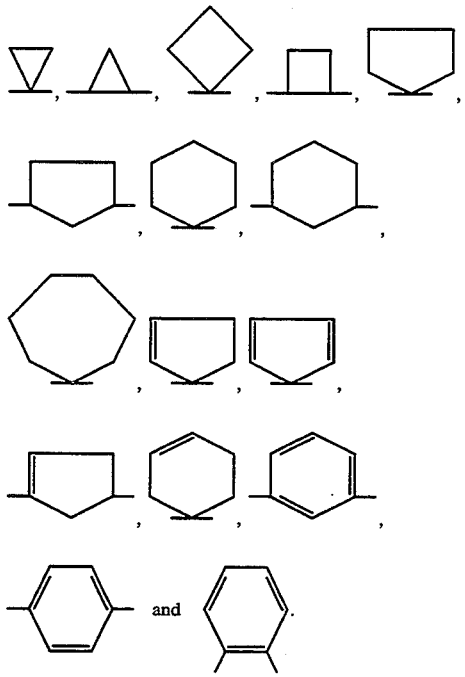

Particularly, the following groups may be used as the common species.

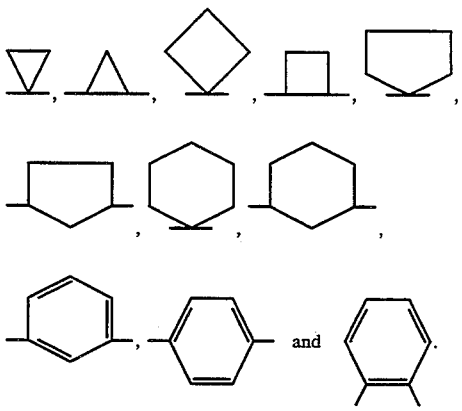

More preferable examples in above groups include the following groups:

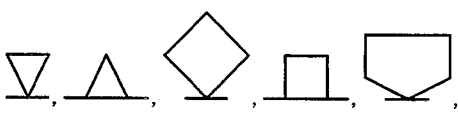

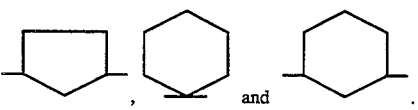

The term '3- to 7-membered heterocyclic ring' means a 3- to 7-membered heterocyclic ring which may contain 1 to 4 hetero-atoms selected from among nitrogen, oxygen, sulfur and other atoms in adidtion to carbon atoms, for instance. Thus, oxetane, tetrahydrofuran, tetrahydropyran, pyrrole, azetidine, pyrrolidine, piperidine, piperazine, tetrahydrothiophene, homopiperidine, morpholine, etc. can be employed.

The divalent group derived from said "3- to 7-membered heterocyclic ring" is a group resulting from either elimination of two hydrogen atoms from a single carbon atom in the 3- to 7-membered heterocyclic ring or elimination of one hydrogen atom from each of two different atoms. Thus, for example, the following groups can be included.

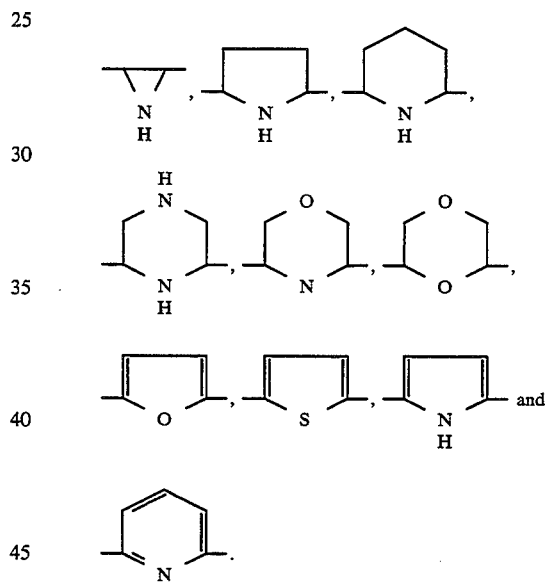

The term "nitrogen-containing heterocyclic group" means a group resulting from elimination of one hydrogen atom from a nitrogen atom in a ring such as a 3- to 13-membered nitrogen-containing heterocyclic ring which contains one nitrogen atom in addition to carbon atoms and which may also contain one to four hetero atoms, for example, selected from nitrogen, oxygen, sulfur and other atoms. Specifically, the following 3- to 9-membered nitrogen-containing heterocyclic groups can be generally used.

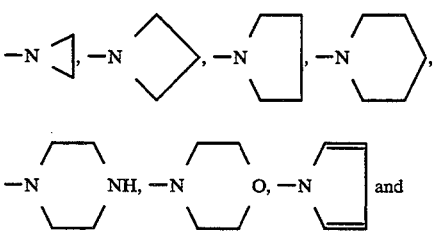

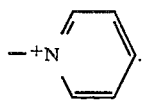

Substituent group(s) by which said '3- to 7-membered homocyclic ring', '3- to 7-membered heterocyclic ring' and 'nitrogen-containing heterocyclic group' may optionally be substituted, may range from 1 to 5 in number and are selected from among an optionally substituted lower alkyl, an optionally substituted amino, hydroxy, carboxyl, nitro, lower alkoxy (e.g. $C_{1-6}$ alkoxy groups such as methoxy, ethoxy, propoxy, etc.), halogen (e.g. fluorine, chlorine, bromine and iodine) and so on. In this connection, substituent group(s) by which the lower alkyl (e.g. $C_{1-6}$ alkyl group such as methyl, ethyl, n-propyl, etc.) mentioned just above may be substituted, may range from 1 to 4 in number and are selected from among hydroxy, amino, mono- or di-lower alkylamino (e.g. mono- or di-$C_{1-6}$ alkylamino groups such as methylamino, ethylamino, propylamino, dimethylamino, diethylamino, etc.), lower alkoxy (e.g. $C_{1-6}$ alkoxy groups such as methoxy, ethoxy, propoxy, hexyloxy, etc.), lower alkylcarbonyloxy (e.g. $C_{1-6}$ alkylcarbonyloxy groups such as acetoxy, ethylcarbonyloxy, etc.), halogen (e.g. fluorine, chlorine, bromine and iodine) and so on. Substituent groups by which the amino group mentioned above may be substituted, may range from 1 to 2 in number and are selected from among $C_{1-6}$ alkyl (e.g. methyl, ethyl, propyl, etc.), acyl (e.g. $C_{1-6}$ acyl groups such as formyl, acetyl, propionyl, butyryl, etc.), 5- to 7-membered cyclic amino (e.g. pyrrolidino, morpholino, piperidino, piperazino, etc.) and so on.

In the formulas presented hereinabove, $R^1$ means a hydrogen atom, an optionally substituted lower alkyl group or a halogen atom. Preferably, $R^1$ may for example be a hydrogen atom or a $C_{1-3}$ alkyl group (e.g. methyl, ethyl, n-propyl, etc.) and is more preferably a hydrogen atom.

$R^2$ and $R^3$ each means a hydrogen atom or an optionally substituted lower alkyl group, or $R^2$ and $R^3$ may, taken together with the adjacent —C=C— group, form a 5- to 7- membered ring. $R^2$ is preferably a hydrogen atom or a $C_{1-3}$ alkyl group (e.g. methyl, ethyl, n-propyl, etc.). $R^2$ is more preferably a hydrogen atom. $R^3$ is preferably a hydrogen atom or a $C_{1-3}$ alkyl group (e.g. methyl, ethyl, n-propyl, etc). $R^3$ is more preferably a $C_{1-3}$ alkyl group (e.g. methyl, ethyl, n-propyl, etc.). Also preferred is the case in which $R^2$ and $R^3$ form a 5- to 7-membered homocyclic ring in combination with the adjacent —C=C— group. Particularly preferred is the case of cyclohexene, benzene or the like.

X represents an oxygen atom or $S(O)_p$ (p means a whole number of 0 to 2). X is preferably an oxygen atom or S and more preferably an oxygen atom.

Y means a group of the formula:

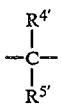

(wherein $R^4$ and $R^5$ each means a hydrogen atom or a lower alkyl group which may be substituted) or a divalent group derived from a 3- to 7-membered homocyclic or heterocyclic ring which may be substituted.

Y is preferably a group of the formula:

$$-\underset{R^{5'}}{\overset{R^{4'}}{\underset{|}{\overset{|}{C}}}}-$$

wherein $R^{4'}$ and $R^{5'}$ each is a hydrogen atom or an optionally substituted $C_{1-3}$ alkyl group. The '$C_{1-3}$ alkyl' of the 'optionally substituted $C_{1-3}$ alkyl group', as represented by $R^{4'}$ and $R^{5'}$, may for example be methyl, ethyl, n-propyl or i-propyl, and the substituent groups by which such $C_{1-3}$ alkyl may be substituted includes the same substituent group(s) as those mentioned for 'lower alkyl'. Particularly preferred are cases in which $R^{4'}$ and $R^{5'}$ each means a hydrogen atom or a $C_{1-3}$ alkyl group (e.g. methyl, ethyl, n-propyl, etc.). $R^{4'}$ and $R^{5'}$ each is more preferably a $C_{1-3}$ alkyl group (e.g. methyl, ethyl, n-propyl, etc.)

Also preferred are cases in which Y is a divalent group derived from a 3- to 7-membered homocyclic ring or heterocyclic ring which may be substituted.

Y is preferably a group of the formula:

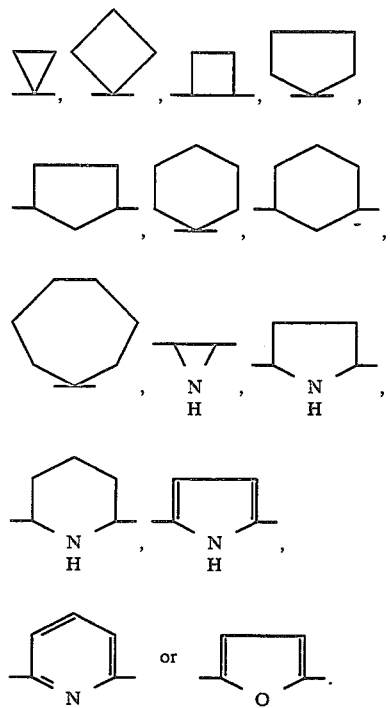

Thus, for example, the following groups can be frequently used as the common species of Y.

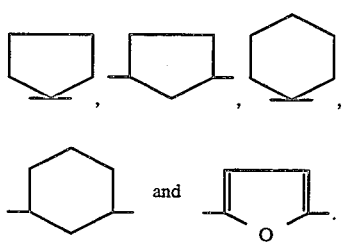

More preferably examples of Y include the follow:

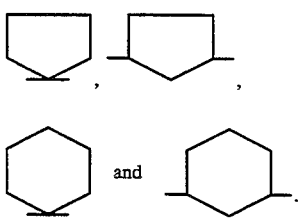

$R^6$ and $R^7$ each is a hydrogen atom, an optionally substituted lower alkyl group, an optionally substituted cycloalkyl group or an optionally substituted aryl group, and $R^6$ and $R^7$ may, taken together with the adjacent nitrogen atom, form a nitrogen-containing heterocyclic group which may be substituted.

$R^6$ and $R^7$ each is preferably a hydrogen atom, a $C_{1-3}$ alkyl group (e.g. methyl, ethyl, n-propyl, etc.) or the like, and particularly a hydrogen atom is preferred.

m stands for a whole number of 0 to 4. It is preferably a whole number of 1 to 4, more preferably a whole number of 1 to 3 and most preferably 1. n stands for a whole number of 0 to 4. It is preferably a whole number of 1 to 4 and more preferably 1. The most useful is the case in which both m and n represent 1.

The salt of compound [I] of the present invention is preferably a physiologically acceptable acid addition salt. Such salts include salt with inorganic acids (e.g., hydrochloric acid, phosphoric acid, hydrobromic acid, sulfuric acid) and salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid). Provided that compound [I] of the present invention has an acidic group, such as —COOH, it may form a salt with an inorganic base (e.g., an alkali metal or alkaline earth metal such as sodium, potassium, calcium or magnesium; or ammonia) or an organic base (e.g., a tri-$C_{1-3}$ alkylamine such as triethylamine).

A method of producing the compound [I] or a salt thereof of the present invention is described below.
Method A) The compound [I] or a salt thereof of the invention can be synthesized by reacting a compound of the general formula:

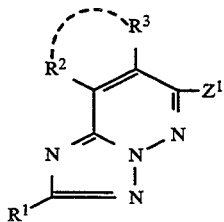 [II]

wherein $Z^1$, $R^1$, $R^2$ and $R^3$ are as defined hereinbefore or a salt thereof with a compound of the general formula:

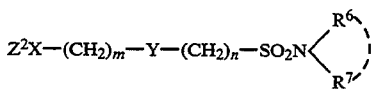 [III]

wherein $Z^2$, X, Y, $R^6$, $R^7$, m and n are as defined hereinbefore or a salt thereof.

The reactive group $Z^1$ may for example be halogen (e.g. chlorine, bromine, iodine, etc.), $C_{6-10}$ arylsulfonyloxy (e.g. benzenesulfonyloxy, p-tolylsulfonyloxy, etc.) or $C_{1-4}$ alkylsulfonyloxy (e.g. methanesulfonyloxy, etc.).

The group which leaves on reacting with $Z^1$, as represented by $Z^2$, may for example be a hydrogen atom or an alkali metal, e.g. sodium, potassium, etc., when X is an oxygen atom or a sulfur atom. When X is —SO— or —$SO_2$, an alkali metal such as sodium, potassium, etc. is employed.

In this reaction, the compound [III] or a salt thereof is used in a proportion of generally 1 to 5 moles and preferably 1 to 2 moles per mole of the compound [II] or a salt thereof.

Generally, this condensation reaction is preferably conducted in the presence of a base, which includes alkali metal hydrides such as sodium hydride, potassium hydride, etc., alkali metal alkoxides such as sodium methoxide, sodium ethoxide, etc., alkali metal hydroxides such as sodium hydroxide, potassium hydroxide, etc., and carbonates such as sodium carbonate, potassium carbonate, etc., to name but a few.

This reaction may be conducted in an inert solvent, e.g. alcohols such as methanol, ethanol, etc., ethers such as dioxane, tetrahydrofuran, etc., aromatic hydrocarbons such as benzene, toluene, xylene, etc., nitriles such as acetonitrile, etc., amides such as dimethylformamide, dimethylacetamide, etc., and sulfoxides such as dimethyl sulfoxide.

The reaction temperature is generally 10° to 200° C. and preferably 50° to 100° C. The reaction time is generally 30 minutes to 24 hours and preferably 1 to 6 hours.

Method B) The compound [I] or a salt thereof of the present invention can also be produced by reacting a compound of the general formula:

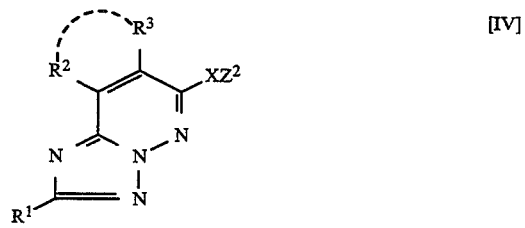 [IV]

wherein $Z^2$, $R^1$, $R^2$, $R^3$ and X are as defined hereinbefore or a salt thereof with a compound of the general formula:

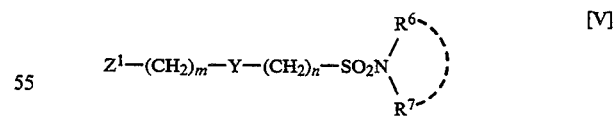 [V]

wherein $Z^1$, Y, $R^6$, $R^7$, m and n are as defined hereinbefore or a salt thereof.

In this reaction, the compound [V] or a salt thereof is used in a proportion of generally 1 to 5 moles and preferably 1 to 2 moles per mole of compound [IV] or a salt thereof.

Generally, this condensation reaction is preferably conducted in the presence of a base which includes alkali metal hydrides such as sodium hydride, potassium hydride, etc., alkali metal alkoxides such as sodium methoxide, sodium ethoxide, etc., alkali metal hydroxides such as sodium hydroxide, potassium hydroxide, etc., and carbonates such as sodium carbonate, potassium carbonate, etc., to name but a few.

This reaction may be conducted in an inert solvent, e.g. alcohols such as methanol, ethanol, etc., ethers such as dioxane, tetrahydrofuran, etc., aromatic hydrocarbons such as benzene, toluene, xylene, etc., nitriles such as acetonitrile, etc., amides such as dimethylformamide, dimethylacetamide, etc. and sulfoxides such as dimethyl sulfoxide.

The reaction temperature is generally 10° to 200° C. and preferably 50° to 150° C. The reaction time is generally 30 minutes to 24 hours and preferably 1 to 10 hours.

Method C) Furthermore, the compound [I] or a salt thereof can be synthesized by reacting a compound of the general formula:

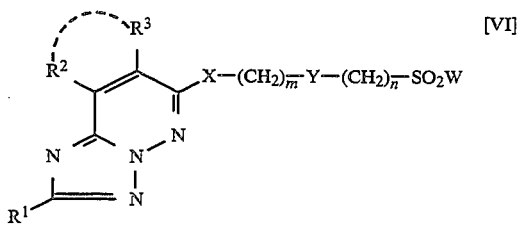

[VI]

wherein W, $R^1$, $R^2$, $R^3$, X, Y, m and n are as defined hereinbefore or a salt thereof with a compound of the general formula:

[VII]

wherein $R^6$ and $R^7$ are as defined hereinbefore or a salt thereof.

The leaving group W may for example be halogen (e.g. chlorine, bromine, iodine, etc.), $C_{6-10}$ arylsulfonyloxy (e.g. benzenesulfonyloxy, p-tolylsulfonyloxy, etc.) or $C_{1-4}$ alkylsulfonyloxy (e.g. methanesulfonyloxy, etc.). Particularly preferred is a halogen atom (e.g. chlorine, bromine, iodine, etc.)

In this reaction, the compound [VII] or a salt thereof is used in a proportion of generally 1 to 5 moles and preferably 1 to 2 moles per mole of the compound [VI] or a salt thereof.

This reaction may be conducted in an inert solvent, e.g. alcohols such as methanol, ethanol, etc., ethers such as dioxane, tetrahydrofuran, etc., aromatic hydrocarbons such as benzene, toluene, xylene, etc., nitriles such as acetonitrile, etc., amides such as dimethylformamide, dimethylacetamide, etc. and sulfoxides such as dimethyl sulfoxide.

The reaction temperature is generally −20° to 100° C. and preferably −10° to 50° C. The reaction time is generally 30 minutes to 5 hours and preferably 1 to 3 hours.

The compound [I] or a salt thereof thus synthesized can be converted, in the per se known manner, to a salt if it is the free form, or to the free form or the other salt if it is a salt. The resulting compound [I] or a salt thereof can be separated and purified from the reaction mixture by the per se known procedures such as solvent extraction, pH adjustment, redistribution, precipitation, crystallization, recrystallization, chromatography and so on. Where the compound [I] or a salt thereof is an optically active compound, it can be separated into d- and l-forms by the conventional procedure for optical resolution.

The Method of producing for the starting compounds [II], [III], [IV], [V], [VI] and [VII], as well as salts thereof, which are used in the production of compound [I] and its salts of the present invention are described below.

As salts of these compounds, there can be used salts with inorganic acids (e.g. hydrochloric acid, phosphoric acid, hydrobromic acid, sulfuric acid, etc.) and salts with organic acids (e.g. acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.). Furthermore, where these compounds have acidic groups such as —COOH, they may form salts with inorganic bases (e.g. alkali metals or alkaline earth metals such as sodium, potassium, calcium, magnesium, etc., ammonia, etc.), or organic bases (e.g. tri-$C_{1-3}$ alkylamines such as triethylamine etc.).

The starting compound [II] or a salt thereof can be synthesized by the process described in J. Org. Chem. 39, 2143 (1987), for instance, or any process analogous thereto.

The starting compound [III] or a salt thereof and the starting compound [V] or a salt thereof can be synthesized by the processes described in Chem. Ber. 91, 2130 (1958), J. Org. Chem. 52, 2162 (1987) and EP-A-381132 for instance, or any process analogous to any of these processes.

The starting compound [IV] or a salt thereof can be produced by the process described in EP-A-381132, for instance, or any process analogous thereto.

The starting compound [VI] or a salt thereof can be synthesized, for example (1) by reacting a compound [II] or a salt thereof with a compound of the general formula:

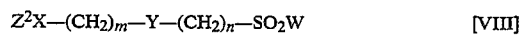

$Z^2X—(CH_2)_m—Y—(CH_2)_n—SO_2W$   [VIII]

wherein X, Y, $Z^2$, W, m and n are as defined hereinbefore or (2) by reacting a compound [IV] or a salt thereof with a compound of the general formula:

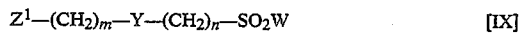

$Z^1—(CH_2)_m—Y—(CH_2)_n—SO_2W$   [IX]

wherein Y, $Z^1$, W, m and n are as defined hereinbefore.

In the above reaction (1), the compound [VIII] or a salt thereof is used in a proportion of generally 1 to 5 moles and preferably 1 to 2 moles per mole of the compound [II] or a salt thereof. This reaction can be conducted in the same manner as the above-mentioned reaction between compound [II] or a salt thereof and compound [III] or a salt thereof.

In the above reaction (2), the compound [IX] or a salt thereof is used in a proportion of generally 1 to 5 moles and preferably 1 to 2 moles per mole of the compound [IV] or a salt thereof. This reaction can be conducted in the same manner as the above-mentioned reaction between compound [IV] or a salt thereof and compound [V] or a salt thereof.

The starting compound [VII] or a salt thereof, the starting compound [VIII] or a salt thereof and the starting compound [IX] or a salt thereof can be respectively produced by the per se known processes or any processes analogous thereto.

The starting compounds and their salts respectively synthesized as above can be isolated and purified by the known procedures such as solvent extraction, pH adjustment, redistribution, precipitation, crystallization, recrystallization, chromatography, etc. but the reaction mixture may be directly used as the starting material for the next process step without prior isolation.

Referring to the reactions according to the present invention and the reactions mentioned just above for synthesis of the starting materials, where the starting compounds have amino, carboxyl and/or hydroxyl groups as a substituent, they may have been previously protected with protective groups which are commonly used in peptide chemistry. In such cases, the objective compound can be obtained by removing the protective groups as necessary after the reactions.

As such amino-protecting groups, there may be used formyl, an optionally substituted $C_{1-6}$ alkyl-carbonyl (e.g. acetyl, ethylcarbonyl, etc.), phenylcarbonyl, $C_{1-6}$ alkyl-oxycarbonyl (e.g. methoxycarbonyl, ethoxycarbonyl, etc.), phenyloxycarbonyl $C_{7-10}$ aralkylcarbonyl (e.g. benzylcarbonyl, etc.), trityl, phthaloyl, N,N-dimethylamino methylene and so on. The substituent groups on these protective groups may range from about 1 to 3 in number and include, among others, a halogen atom (e.g. fluorine, chlorine, bromine and iodine), $C_{1-6}$ alkyl-carbonyl (e.g. methylcarbonyl, ethylcarbonyl, butylcarbonyl, etc.), nitro and so on.

The carboxy-protecting group includes an optionally substituted $C_{1-6}$ alkyl (e.g. methyl, ethyl, n-propyl, i-propyl, n-butyl, tert-butyl, etc.), phenyl, trityl, silyl and other groups. The substituents on these protective groups may range from about 1 to 3 in number and include, among others, a halogen atom (e.g. fluorine, chlorine, bromine and iodine), formyl, $C_{1-6}$ alkyl-carbonyl (e.g. acetyl, ethylcarbonyl, butylcarbonyl, etc.) and nitro.

The hydroxy-protecting group includes an optionally substituted $C_{1-6}$ alkyl (e.g. methyl, ethyl, n-propyl, i-propyl, n-butyl, tert-butyl, etc.), phenyl, $C_{7-10}$ aralkyl (e.g. benzyl, etc.), formyl, $C_{1-6}$ alkylcarbonyl (e.g. acetyl, ethylcarbonyl, etc.), phenyloxycarbonyl, $C_{7-10}$ aralkyl-carbonyl (e.g. benzylcarbonyl, etc.), pyranyl, furanyl, silyl and other groups. The substituents on these protective groups may range from about 1 to 4 in number and are selected from among a halogen atom (e.g. fluorine, chlorine, bromine and iodine), $C_{1-6}$ alkyl (e.g. methyl, ethyl, n-propyl, etc.), phenyl, $C_{7-10}$ aralkyl (e.g. benzyl, etc.), nitro and so on.

For elimination of these protective groups, the per se known procedures or any procedures analogous thereto can be utilized. Such procedures involve the use of an acid or a base, reduction, UV irradiation, treatment with hydrazine, phenylhydrazine, sodium N-methyldithiocarbamate, tetrabutylammonium fluoride or palladium acetate and so on.

Compound [I] of this invention or a salt thereof possesses excellent antiallergic, antiinflammatory and anti-PAF (platelet activating factor) activities and can be used safely (acute toxicity: $LD_{50} > 2g/kg$) as an anti-asthmatic agent in mammals (e.g., humans, mice, dogs, rats, bovines). Although compound [I] of the present invention or a salt thereof may be used as such in the form of bulk powder, it is a common practice to administer it in the form of a preparation along with pharmaceutical carriers. Example preparations include tablets, capsules, granules, fine granules, powders, syrups, injections and inhalations. These preparations are prepared in accordance with a conventional method. Examples of carriers for oral preparations include those commonly used in the pharmaceutical industry, such as starch, mannitol, crystalline cellulose and carboxymethylcellulose sodium. Examples of carriers for injections include distilled water, physiological saline, glucose solutions and transfusions. Other additives used commonly in pharmaceutical preparations may be added as appropriate. Although the dose of these preparations varies depending on age, body weight, symptoms, route and frequency of administration and other factors, they may be administered at 0.1 to 100 mg/kg, preferably 1 to 50 mg/kg, more preferably 1 to 10 mg/kg, in one to two portions daily for an adult. Route of administration may be oral or parenteral.

In the following, the Examples, Reference Examples, Formulation Examples and Experiment are merely intended to describe the present invention in further detail and should by no means be construed as defining the metes and bounds of the invention.

Detection of the fractions containing each object compound in the examples was carried out under TLC (thin layer chromatography) monitoring. In TLC monitoring, Merck's 60F$_{254}$ was used as the TLC plate and a UV detector for detection. Further, room temperature means 15° to 20° C.

Abbreviations used in the following have the following meanings.

J: coupling constant
s: singlet
bs: broad singlet
t: triplet
m: multiplet
Hz: hertz
d: doublet
q: quartet
NMR: Nuclear Magnetic Resonance
DMSO: Dimethyl sulfoxide
CDCl$_3$: deuteriochloroform
v/v: volume/volume
%: weight %
m.p.: melting point
i.v.: intravenous injection
δ(ppm): chemical shift (part per million)

EXAMPLE 1

Production of 6-(2,2-dimethyl-3-sulfamoyl-1-propoxy)[1,2,4]-triazolo[1,5-b]pyridazine In 15 ml of dimethylformamide was suspended 0.42 g of 60% sodium hydride in oil, followed by addition of 0.878 g of 3-hydroxy-2,2-dimethyl-1-propanesulfonamide and the mixture was stirred under reduced pressure at room temperature for 30 minutes. Then, 0.773 g of 6-chloro[1,2,4]triazolo[1,5-b]pyridazine was added and the mixture was further stirred at room temperature for 1 hour. Following addition of 40 ml of iced water, the reaction mixture was adjusted to pH 6 with 1N-hydrochloric acid and the resulting crystals were collected by filtration and washed with 20 ml of water and 20 ml of ethyl ether. The washed crystals were recrystallized from hot ethanol to provide 1.16 g of the title compound. m.p. 181°–184° C.

Elemental analysis for $C_{10}H_{15}N_5O_3S$ Calcd. (%); C, 42.10; H, 5.30; N, 24.55 Found (%): C, 41.87; H, 5.28; N, 24.59

EXAMPLE 2

Production of
6-(2,2-diethyl-3-sulfamoyl-1propoxy)[1,2,4]triazolo[1,5-b]pyridazine In 20 ml of dimethylformamide was suspended 0.64 g of 60% sodium hydride in oil, followed by addition of 1.56 g of 3-hydroxy-2,2-diethyl-1-propanesulfonamide and the mixture was stirred under reduced pressure at room temperatue for 30 minutes. Then, 1.24 g of 6-chloro[1,2,4]triazolo[1,5-b]pyridazine was added and the mixture was further stirred at room temperature for 1.5 hours. Following addition of 100 ml of iced water, the reaction mixture was adjusted to pH 6 with 1N-hydrochloric acid and the resulting crystals were collected by filtration and washed with 20 ml of water and 20 ml of ethyl ether. The washed crystals were recrystallized from hot ethanol to provide 1.57 g of the title compound. m.p. 194°–197° C.

Elemental analysis for $C_{12}H_{19}N_5O_3S.0.5EtOH$ Calcd. (%): C, 46.41; H, 6.59; N, 20.82 Found (%): C, 46.33; H, 6.68; N, 20.99

EXAMPLE 3

Production of
6-(2,2-dimethyl-3-sulfamoyl-1-propoxy)-7-methyl[1,2,4]triazolo[1,5-b]pyridazine In 5 ml of tetrahydrofuran was dissolved 0.44 g of 3-hydroxy-2,2-dimethyl-1-propanesulfonamide, followed by addition of 0.5 ml of N,N-dimethylformamide dimethyl acetal. The mixture was allowed to stand at room temperature for 10 hours, after which it was concentrated under reduced pressure. The residue was dissolved in 4 ml of dimethylformamide, and following addition of 0.2 g of 60% sodium hydride in oil, the solution was stirred under reduced pressure at room temperature for 30 minutes. Then, 0.37 g of 6-chloro-7-methyl[1,2,4]triazolo[1,5-b]pyridazine was added and the mixture was stirred at room temperature for 1 hour. Following addition of 50 ml of ice-water and 30 ml of 1N-hydrochloric acid, the reaction mixture was refluxed for 1 hour and adjusted to pH 6 with sodium bicarbonate. The resulting crystals were collected by filtration and recrystallized from aqueous methanol to provide 0.12 g of the title compound. m.p. 216°–218° C.

Elemental analysis for $C_{11}H_{17}N_5O_3S$ Calcd. (%): C, 44.14; H, 5.72; N, 23.39 Found (%): C, 44.13; H, 5.74; N, 23.19

EXAMPLE 4

Production of
7,8-dimethyl-6-(2,2-dimethyl-3-sulfamoyl-1-propoxy)[1,2,4]triazolo[1,5-b]pyridazine In 30 ml of dimethylformamide was suspended 1.38 g of 60% sodium hydride in oil, followed by addition of 2.51 g of 3-hydroxy-2,2-dimethyl-1-propanesulfonamide and the mixture was stirred under reduced pressure at room temperature for 1 hour. To this was added 2.56 g of 6-chloro-7,8-dimethyl[1,2,4]triazolo[1,5-b]pyridazine and the mixture was stirred at room temperature for 3 hours. Following addition of 100 ml of iced water, the reaction mixture was adjusted to pH 6 with 5N-hydrochloric acid and extracted with 3 portions of ethyl acetate-tetrahydrofuran (2:1). The extract was washed with 20 ml of saturated aqueous solution of sodium chloride and dried over anhydrous magnesium sulfate. The solvent was then distilled off under reduced pressure and the residue was subjected to silica gel column chromatography, elution being carried out with dichloromethane-methanol (30:1). The fractions containing the desired product were pooled and concentrated to provide 0.63 g of the title compound. m.p. 175°–177° C.

Elemental analysis for $C_{12}H_{19}N_5O_3S$ Calcd. (%): C, 45.99; H, 6.11; N, 22.35 Found (%): C, 46.27; H, 6.14; N, 22.16

EXAMPLE 5

Production of
6-(2,2-diethyl-3-sulfamoyl-1-propoxy)-7-methyl[1,2,4]-triazolo[1,5-b]pyridazine In 20 ml of dimethylformamide was suspended 0.672 g of 60% sodium hydride in oil, followed by addition of 1.72 g of 3-hydroxy-2,2-diethyl-1-propanesulfonamide and the mixture was stirred under reduced pressure at room temperature for 1 hour. To this was added 1.35 g of 6-chloro-7-methyl[1,2,4]triazolo[1,5-b]pyridazine and the mixture was stirred under a nitrogen atmosphere at room temperature for 2 hours. Following addition of 70 ml of iced water, the reaction mixture was adjusted to pH 6 with 5N-hydrochloric acid and extracted with 3 portions of ethyl acetate-tetrahydrofuran (2:1). The extract was washed with saturated aqueous solution of sodium chloride and dried over anhydrous magnesium sulfate. The solvent was then distilled off under reduced pressure and the residue was subjected to silica gel column chromatography, elution being carried out with dichloromethane-ethyl acetate-methanol (10:10:1). The fractions containing the object product were pooled and concentrated, and 50 ml of 5N-hydrochloric acid was added to the residue. The mixture was refluxed for 30 minutes. After cooling, the mixture was concentrated under reduced pressure and the residue was diluted with water and aqueous solution of sodium hydrogen carbonate and extracted with 3 portions of ethyl acetate-tetrahydrofuran (1:1). The extract was washed with saturated aqueous solution of sodium chloride once, dried over anhydrous magnesium sulfate and concentrated under reduced pressure. The residue was recrystallized from hot ethanol to provide 0.79 g of the title compound. m.p. 189°–192° C.

Elemental analysis for $C_{13}H_{21}N_5O_3S.0.5EtOH$ Calcd. (%): C, 47.98; H, 6.90; N, 19.90 Found (%): C, 47.44; H, 6.84; N, 19.93

EXAMPLE 6

Production of
6-(2,2-diethyl-3-sulfamoyl-1-propoxy)-7-methyl[1,2,4]-triazolo[1,5-b]pyridazine To a solution of 1.38 g of 3-(N,N-dimethylaminomethylene)aminosulfonyl-2,2-diethyl-1-propanol in 30 ml of tetrahydrofuran was added 0.23 g of 60% sodium hydride in oil and the mixture was stirred at room temperature for 1 hour. To this reaction mixture was added 0.74 g of 6-chloro-7-methyl[1,2,4]triazolo[1,5-b]pyridazine and the mixture was refluxed with stirring for 1 hour. After cooling, the reaction mixture was adjusted to pH 6 with 1N-hydrochloric acid and extracted with ethyl acetate-tetrahydrofuran (1:1). The extract was washed with water and dried and the solvent was distilled off. To the residue was added 14 ml of 6N-hydrochloric acid and the mixture was stirred at 110° C. for 30 minutes. After cooling, 100 ml of water was added to the reaction mixture and the resulting crystals were recovered by filtration and recrystallized from methanol to provide 1.16 g of the title compound. m.p. 208°–209° C.

Elemental analysis for $C_{13}H_{21}N_5O_3S$ Calcd. (%): C, 47.69; H, 6.46; N, 21.39 Found (%): C, 47.46; H, 6.44; N, 21.59

Recrystallization of this product from hot ethanol gave the crystals containing ethanol as obtained in Example 5.

EXAMPLE 7

Production of 6-(2,2-dimethyl-4-sulfamoyl-1-butoxy)-7-methyl[1,2,4]triazolo[1,5-b]pyridazine Using 4-hydroxy-3,3-dimethyl-1-butanesulfonamide and 6-chloro-7-methyl[1,2,4]triazolo[1,5-b]pyridazine, the same reaction was conducted as in Example 5 to produce the title compound. m.p. 214°–215° C.

Elemental analysis for $C_{12}H_{19}N_5O_3S$ Calcd. (%): C, 45.99; H, 6.11; N, 22.35 Found (%): C, 45.80; H, 5.91; N, 22.56

NMR (d$_6$-DMSO) δ: 1.06 (6H, s), 1.80–1.95 (2H, m), 2.33 (3H, s), 2.97–3.09 (2H, m), 4.09 (2H, s), 6.75 (2H, s), 8.16 (1H, s), 8.38 (1H, s)

EXAMPLE 8

Production of 6-(2,2-dimethyl-5-sulfamoyl-1-pentyloxy)-7-methyl[1,2,4]triazolo[1,5-b]pyridazine Using 5-hydroxy-4,4-dimethyl-1-pentanesulfonamide and 6-chloro-7-methyl[1,2,4]triazolo[1,5-b]pyridazine, the same reaction was conducted as in Example 5 to produce the title compound. m.p. 171°–172° C.

Elemental analysis for $C_{13}H_{21}N_5O_3S$ Calcd. (%): C, 47.69; H, 6.46; N, 21.39 Found (%): C, 47.45; H, 6.39; N, 21.18

NMR (CDCl$_3$) δ: 1.05 (6H, s), 1.45–1.59 (2H, m), 1.66–1.82 (2H, m), 2.33 (3H, s), 2.96 (2H, t, J=7.8 Hz), 4.08 (2H, s), 6.72 (2H, bs), 8.15 (1H, s), 8.37 (1H, s)

EXAMPLE 9

Production of 6-(2,2-dimethyl-6-sulfamoyl-1-hexyloxy)-7-methyl[1,24]triazolo[1,5-b]pyridazine Using 6-hydroxy-5,5-dimethyl-1-hexanesulfonamide and 6-chloro-7-methyl[1,2,4]triazolo[1,5-b]pyridazine, the same reaction was conducted as in Example 5 to produce the title compound. m.p. 161°–163° C.

Elemental analysis for $C_{14}H_{23}N_5O_3S$ Calcd. (%): C, 49.25; H, 6.79; N, 20.51 Found (%): C, 48.99; H, 6.68; N, 20.74

NMR (d$_6$-DMSO) δ: 1.05 (6H, s), 1.38–1.60 (4H, m), 1.67–1.98 (4H, m), 2.37 (3H, s), 3.15 (2H, t, J=7.8 Hz), 4.14 (2H, s), 4.77 (2H, bs), 7.78 (1H, s), 8.25 (1H, s)

EXAMPLE 10

Production of 6-(2,2-diethyl-6-sulfamoyl-1-hexyloxy)-7-methyl[1,2,4]triazolo[1,5-b]pyridazine Using 6-hydroxy-5,5-diethyl-1-hexanesulfonamide and 6-chloro-7-methyl[1,2,4]triazolo[1,5-b]pyridazine, the same reaction was conducted as in Example 5 to produce the title compound. m.p. 132°–133° C.

Elemental analysis for $C_{16}H_{27}N_5O_3S$ Calcd. (%): C, 52.01; H, 7.37; N, 18.95 Found (%): C, 51.89; H, 7.10; N, 19.08

NMR (CDCl$_3$) δ: 0.85 (6H, t, J=7.4 Hz), 1.35–1.55 (8H, m), 1.78–1.98 (2H, m), 3.13 (2H, t, J=8.0 Hz), 4.18 (2H, s), 4.76 (2H, bs), 7.77 (1H, s), 8.25 (1H, s)

EXAMPLE 11

Production of 6-(2,2-diethyl-5-sulfamoyl-1-pentyloxy)-7-methyl[1,2,4]triazolo[1,5-b]pyridazine Using 5-hydroxy-4,4-diethyl-1-pentanesulfonamide and 6-chloro-7-methyl[1,2,4]triazolo[1,5-b]pyridazine, the same reaction was conducted as in Example 5 to produce the title compound. m.p. 157°–158° C.

NMR (CDCl$_3$) δ: 0.86 (6H, t, J=7.4 Hz), 1.46 (4H, q, J=7.4Hz), 1.48 (2H, t, J=7.6 Hz), 1.79–1.98 (2H, m), 2.36 (3H, s), 3.07 (2H, t, J=7.6 Hz), 4.21 (2H, s), 5.54 (2H, bs), 7.76 (1H, s), 8.24 (1H, s)

EXAMPLE 12

Production of 6-(2,2-diethyl-4-sulfamoyl-1-butoxy)-7-methyl[1,2,4]triazolo[1,5-b]pyridazine Using 4-(N,N-dimethylaminomethylene)aminosulfonyl-2,2-diethyl-1-butanol and 6-chloro-7-methyl[1,2,4]triazolo[1,5-b]pyridazine, the same reaction as in Example 6 was conducted to produce the title compound. m.p. 148°–149° C.

Elemental analysis: for $C_{14}H_{23}N_5O_3S$ Calcd. (%): C, 49.25; H, 6.79; N, 20.51 Found (%): C, 48.99; H, 6.68; N, 20.24

NMR (d$_6$-DMSO) δ: 0.84 (6H, t, J=7.0 Hz), 1.42 (4H, q, J=7.0 Hz), 1.76–1.91 (2H, m), 2.31 (3H, s), 2.89–3.03 (2H, m), 4.11 (2H, s), 6.77 (2H, bs), 8.15 (1H, s), 8.39 (1H, s)

EXAMPLE 13

Production of 6-(2,2-pentamethylene-3-sulfamoyl-1-propoxy)-7-methyl[1,2,4]triazolo[1,5-b]pyridazine Using 3-(N,N-dimethylaminomethylene)aminosulfonyl-2,2-pentamethylene-1-propanol and 6-chloro-7-methyl[1,2,4]triazolo[1,5-b]pyridazine, the same reaction as in Example 6 was conducted to produce the title compound. m.p. 268°–270° C.

Elemental analysis for $C_{14}H_{21}N_5O_3S$ Calcd. (%): C, 49.54; H, 6.24; N, 20.63 Found (%): C, 49.19; H, 6.22; N, 20.40

NMR (d$_6$-DMSO) δ: 1.28–1.89 (10H, m), 2.34 (3H, s), 3.34 (2H, s), 4.43 (2H, s), 6.94 (2H, bs), 8.16 (1H, s), 8.39 (1H, s)

EXAMPLE 14

Production of 6-(3,3-dimethyl-5-sulfamoyl-1-pentyloxy)-7-methyl[1,2,4]triazolo[1,5-b]pyridazine Using 5-(N,N-dimethylaminomethylene)aminosulfonyl-3,3-dimethyl-1-pentanol and 6-chloro-7-methyl[1,2,4]triazolo[1,5-b]pyridazine, the same reaction as in Example 6 was conducted to produce the title compound. m.p. 143°–144° C.

Elemental analysis: for $C_{13}H_{21}N_5O_3S$ Calcd. (%): C, 47.69; H, 6.46; N, 21.39 Found (%): C, 47.50; H, 6.53; N, 21.13

NMR (d$_6$-DMSO) δ: 1.00 (6H, s), 1.66–1.89 (4H, m), 2.30 (3H, s), 2.94–3.10 (2H, m), 4.43 (2H, t, J=6.8. Hz), 6.77 (2H, bs), 8.16 (1H, s), 8.39 (1H, s)

EXAMPLE 15

Production of 6-(4,4-dimethyl-6-sulfamoyl-1-hexyloxy)-7-methyl[1,2,4]triazolo[1,5-b]pyridazine Using 6-(N,N-dimethylaminomethylene)aminosulfonyl-4,4-dimethyl-1-hexanol and 6-chloro-7-methyl[1,2,4]triazolo[1,5-b]pyridazine, the same reaction as in Example 6 was conducted to produce the title compound. m.p. 154°–155° C.

Elemental analysis for $C_{14}H_{23}N_5O_3S$ Calcd. (%): C, 49.25; H, 6.79; N, 20.51 Found (%): C, 48.98; H, 7.02; N, 20.86

NMR (d$_6$-DMSO) δ: 0.91 (6H, s), 1.29–1.46 (2H, m), 1.57–1.88 (4H, m), 2.30 (3H, s), 2.85–3.04 (2H, m), 4.35 (2H, t, J=6.3 Hz), 6.75 (2H, bs), 8.15 (1H, s), 8.37 (1H, s)

EXAMPLE 16

Production of 6-(2,2-pentamethylene-4-sulfamoyl-1-butoxy)-7-methyl[1,2,4]triazolo[1,5-6]pyridazine Using 4-(N,N-dimethylaminomethylene)aminosulfonyl-2,2-pentamethylene-1-butanol and 6-chloro-7-methyl[1,2,4]triazolo[1,5-b]pyridazine, substantially the same reaction as in Example 6 was conducted to produce the title compound. m.p. 208°–209° C.

Elemental analysis for $C_{15}H_{23}N_5O_3S$ Calcd. (%): C, 50.97; H, 6.56; N, 19.81 Found (%): C, 51.24; H, 6.55; N, 19.58

NMR (d$_6$-DMSO) δ: 1.32–1.65 (10H, m), 1.86–2.03 (2H, m), 2.32 (3H, s), 2.90–3.04 (2H, m), 4.16 (2H, s), 6.75 (2H, bs), 8.14 (1H, s), 8.38 (1H, s)

EXAMPLE 17

Production of 6-(2-isopropyl-3-sulfamoyl-1-propoxy)-7-methyl[1,2,4]-triazolo[1,5-b]pyridazine Using 3-(N,N-dimethylaminomethylene)aminosulfonyl-2-isopropyl-1-propanol and 6-chloro-7-methyl[1,2,4]triazolo[1,5-b]pyridazine, the same reaction as in Example 6 was conducted to produce the title compound. m.p. 196°–197° C.

Elemental analysis for $C_{12}H_{19}N_5O_3S$ Calcd. (%): C, 45.99; H, 6.11; N, 22.35 Found (%): C, 45.85; H, 6.18; N, 22.00

NMR (d$_6$-DMSO) δ: 0.97 (3H, d, J=6.8 Hz), 0.98 (3H, d, J=6.8 Hz), 1.98–2.19 (1H, m), 2.25–2.43 (1H, m), 2.31 (3H, s), 3.03–3.27 (2H, m), 4.40–4.59 (2H, m), 6.93 (2H, bs), 8.16 (1H, s), 8.39 (1H, s)

EXAMPLE 18

Production of 6-(2-ethyl-2-methyl-3-sulfamoyl-1-propoxy)-7-methyl[1,2,4]triazolo[1,5-b]pyridazine Using 3-(N,N-dimethylaminomethylene)aminosulfonyl-2-ethyl-2-methyl-1-propanol and 6-chloro-7-methyl[1,2,4]triazolo[1,5-b]pyridazine, the same reaction as in Example 6 was conducted to produce the title compound. m.p. 189°–190° C.

Elemental analysis for $C_{12}H_{19}N_5O_3S$ Calcd. (%): C, 45.99; H, 6.11; N, 22.35 Found (%): C, 46.17; H, 6.18; N, 22.19

NMR (d$_6$-DMSO) δ: 0.90 (3H, t, J=7.4 Hz), 1.20 (3H, s), 1.66 (2H, q, J=7.4 Hz), 2.34 (3H, s), 3.22 (2H, d, J=3.6 Hz), 4.31 (2H, s), 6.93 (2H, bs), 8.16 (1H, s), 8.39 (1H, s)

EXAMPLE 19

Production of 6-(2,2-diethyl-3-sulfamoyl-1-propoxy)-2,7-dimethyl[1,2,4]triazolo[1,5-b]pyridazine Using 3-(N,N-dimethylaminomethylene)aminosulfonyl-2,2-diethyl-1-propanol and 6-chloro-2,7-dimethyl[1,2,4]triazolo[1,5-b]pyridazine, the same reaction as in Example 6 was conducted to produce the title compound. m.p. 221°–222° C.

Elemental analysis: for $C_{14}H_{23}N_5O_3S$ Calcd. (%): C, 49.25; H, 6.79; N, 20.51 Found (%): C, 49.36; H, 6.56; N, 20.71

NMR (d$_6$-DMSO) δ: 0.88 (6H, t, J=7.2 Hz), 1.62 (4H, q, J=7.2 Hz), 2.31 (3H, s), 2.49 (3H, s), 3.21 (2H, s), 4.31 (2H, s), 6.93 (2H, bs), 8.02 (1H, s)

EXAMPLE 20

Production of 2,7-dimethyl-6-(2,2-dimethyl-3-sulfamoyl-1-propoxy)[1,2,4]triazolo[1,5-b]pyridazine Using 3-(N,N-dimethylaminomethylene)aminosulfonyl-2,2-dimethyl-1-propanol and 6-chloro-2,7-dimethyl[1,2,4]trizolo[1,5-b]pyridazine, the same reaction as in Example 6 was conducted to produce the title compound. m.p. 217°–218° C.

Elemental analysis for $C_{12}H_{19}N_5O_3S$ Calcd. (%): C, 45.99; H, 6.11; N, 22.35 Found (%) : C, 46.02; H, 5.99; N, 22.36

EXAMPLE 21

Production of 6-(2-ethyl-2-methyl-3-sulfamoyl-1-propoxy)-2,7-dimethyl[1,2,4]triazolo[1,5-b]pyridazine Using 3-(N,N-dimethylaminomethylene)aminosulfonyl-2-ethyl-2-methyl-1-propanol and 6-chloro-2,7-dimethyl[1,2,4]triazolo[1,5-b]pyridazine, the same reaction as in Example 6 was conducted to produce the title compound. m.p. 194°–195° C.

Elemental analysis for $C_{13}H_{21}N_5O_3S$ Calcd. (%): C, 47.69; H, 6.46; N, 21.39 Found (%): C, 47.63; H, 6.32; N, 21.57

EXAMPLE 22

Production of 6-(2,2-diethyl-3-sulfamoyl-1-propoxy)-2,8-dimethyl[1,2,4]triazolo[1,5-b]pyridazine Using 3-(N,N-dimethylaminomethylene)aminosulfonyl-2,2-diethyl-1-propanol and 6-chloro-2,8-dimethyl[1,2,4]triazolo[1,5-b]pyridazine, the same reaction as in Example 6 was conducted to produce the title compound. m.p. 159°–160° C.

Elemental analysis for $C_{14}H_{23}N_5O_3S$ Calcd. (%): C, 49.25; H, 6.79; N, 20.51 Found (%): C, 49.04; N, 6.65; N, 20.36

EXAMPLE 23

Production of 2,7-dimethyl-6-(2,2-pentamethylene-4-sulfamoyl-1-butoxy)[1,2,4]triazolo[1,5-b]pyridazine Using 4-(N,N-dimethylaminomethylene)aminosulfonyl-2,2-pentamethylene-1-butanol and 6-chloro-2,7-dimethyl[1,2,4]triazolo[1,5-b]pyridazine, the same reaction as in Example 6 was conducted to produce the title compound. m.p. 204°–205° C.

Elemental analysis for $C_{16}H_{25}N_5O_3S$ Calcd. (%) : C, 52.30; H, 6.86; N, 19.06 Found (%) : C, 52.45; H, 6.90; N, 18.78

EXAMPLE 24

Production of 6-(3-sulfamoyl-1-propoxy)[1,2,4]triazolo[1,5-b]pyridazine

In 12 ml of dimethylformamide was suspended 0.48 g of 60% sodium hydride in oil followed by addition of 0.835 g of 3-hydroxy-1-propanesulfonamide and the mixture was stirred under reduced pressure at room temperature for 30 minutes. Then, 0.928 g of 6-chloro[1,2,4]triazolo[1,5-b]pyridazine was added and the mixture was further stirred at room temperature for 18 hours. Following addition of 40 ml of ice water, the reaction mixture was adjusted to pH6 with 1N-hydrochloric acid then saturated with sodium chloride. The aqueous layer was extracted with tetrahydrofuran and the extract was dried over magnesium sulfate. The solvent was distilled off under reduced pressure and the resulting residue was crystallized from ethyl ether. The washed crystals were recrystallized from hot methanol to provide 0.811 g of title compound. m.p. 145°–147° C.

Elemental analysis for $C_8H_{11}N_5O_3S$ Calcd. (%): C, 37.35; H, 4.31; N, 27.22 Found (%): C, 37.48; H, 4.33; N, 26.95

EXAMPLE 25

Production of 6-[3-(N,N-dimethylsulfamoyl)-1-propoxy][1,2,4]-triazolo[1,5-b]pyridazine In 10 ml of dimethylformamide was suspended 0.252 g of 60% sodium hydride in oil followed by addition of 1.0 g of N,N-dimethyl-3-hydroxypropane-1-sulfonamide and the mixture was stirred under reduced pressure at room temperature for 30 minutes. Then, 0.928 g of 6-chloro[1,2,4]triazolo[1,5-b]pyridazine was added and the mixture was further stirred at room temperature for 1.5 hours. Following addition of 30 ml of ice water, the reaction mixture was adjusted to pH 4.0 with 1N-hydrochloric acid and the resulting crystals were collected by filtration and recrystallized from hot methanol to provide 1.255 g of the title compound. m.p. 151°–153° C.

Elemental analysis for $C_{10}H_{15}N_5O_3S$ Calcd. (%) : C, 42.10; H, 5.30; N, 24.55 Found (%): C, 42.17; H, 5.21; N, 24.69

EXAMPLE 26

Production of 6-[3-(1-methyl-4-piperazinylsulfonyl)-1-propoxy][1,2,4]triazolo[1,5-b]pyridazine In 10 ml of dimethylformamide was suspended 0.21 g of 60% sodium hydride in oil followed by addition of 1.12 g of 3-(1-methyl-4-piperazinylsulfonyl)-1-propanol and the mixture was stirred under reduced pressure at room temperature for 75 minutes. Then, 0.773 g of 6-chloro[1,2,4]triazolo[1,5-b]pyridazine was added and the mixture was further stirred at room temperature for 1.5 hours. Following addition of 40 ml of ice water, the reaction mixture was saturated with sodium chloride. The aqueous layer was extrated with tetrahydrofuran and the extrat was dried over magnesium sulfate. The solvent was then distilled off under reduced pressure and the residue was subjected to silica gel column chromatography, elution being carried out with dichloromethane-methanol (10:1). The fractions containing the desired product were pooled and concentrated to provide 1.032 g of the title compound. m.p. 140°–141° C.

Elemental analysis for $C_{13}H_{20}N_6O_3S$ Calcd. (%): C, 45.87; H, 5.92; N, 24.69 Found (%): C, 45.67; H, 5.94; N. 24.90

EXAMPLE 27

Production of 6-(3-sulfamoyl-1-propylthio)[1,2,4]triazolo[1,5-b]pyridazine

In 20 ml of methanol was dissolved 1.94 ml of methyl 3-mercaptopropionate followed by addition of 7.5 ml of 2N sodium methoxide in methanol and 0.773 g of 6-chloro[1,2,4]triazolo[1,5-b]pyridazine. The solution was refluxed for 30 minutes. After cooling, the mixture was concentrated under reduced pressure. To the residue was added ethyl acetate and the resulting crystals were collected by filtration. In 20 ml of tetrahydrofuran were suspended the crystals followed by addition of 0.997 g of 3-iodopropane-1-sulfonamide and the mixture was refluxed for 2.5 hours. After cooling, the solvent was distilled off under reduced pressure and the residue was treated with 20 ml of ice water and adjusted to pH 4 with 1N-hydrochloric acid. The resulting crystals were collected by filtration and recrystallized from methanol to provide 0.856 g of the title compound. m.p. 130°–131° C.

Elemental analysis for $C_8H_{11}N_5O_2S_2$ Calcd. (%): C, 35.15; N, 4.06; N, 25.62 Found (%): C, 35.17; N. 4.06; N, 25.55

REFERENCE EXAMPLE 1

Production of ethyl 4-chloro-2,2-dimethylbutyrate

To a solution of 22.2 ml of diisopropylamine in 150 ml of tetrahydrofuran was added 93.6 ml of 1.6M n-butyllithium-hexane with stirring at −5° to 0° C. and the mixture was stirred for 30 minutes. The reaction mixture was cooled to −78° C. and 19.0 ml of ethyl isobutyrate was added dropwise. The mixture was then further stirred for 45 minutes, after which a solution of 11.9 ml of 1-bromo-2-chloroethane in 10 ml of tetrahydrofuran was added dropwise. The reaction mixture was stirred at −78° C. for 1 hour and, then, at room temperature for 2 hours. After an excess amount of an aqueous solution of ammonium chloride was added, the mixture was extracted with ethyl acetate. The extract was washed with water and dried ($MgSO_4$) and the solvent was distilled off. Finally, the residue was distilled under reduced pressure to provide 24.7 g of the title compound as colorless oil. b.p. 54°–56° C./0.25 mmHg NMR ($CDCl_3$) δ: 1.22 (6H, s), 1.26 (3H, t, J=7.0Hz), 2.06 (2H, t, J=8.1 Hz), 3.51 (2H, t, J=8.1 Hz), 4.14 (2H, q, J=7.0 Hz)

REFERENCE EXAMPLE 2

Production of ethyl 2,2-dimethyl-4-thiocyanobutyrate

In 100 ml of dimethylformamide were dissolved 22.1 g of ethyl 4-chloro-2,2-dimethylbutyrate and 14.5 g of potassium thiocyanate and the solution was stirred at 100° C. for 7 hours. The reaction mixture was poured in 500 ml of water and extracted with ethyl ether. The extract was washed with water and dried ($MgSO_4$) and the solvent was distilled off. The residue was subjected to vacuum distillation to provide 16.4 g of the title compound as colorless oil. b.p. 109°–111° C./0.3 mmHg NMR (CDCl$_3$) δ: 1.24 (6H, s), 1.27 (3H, t, J=7.2 Hz), 2.00–2.12 (2H, m), 2.86–2.97 (2H, m), 2.86–2.97 (2H, m), 4.15 (2H, q, J=7.2 Hz).

REFERENCE EXAMPLE 3

Production of ethyl 4-aminosulfonyl-2,2-dimethylbutyrate

In a mixture of 200 ml of acetic acid and 200 ml of water was dissolved 42.5 g of ethyl 2,2-dimethyl-4-thiocyanobutyrate and while the solution was vigorously stirred, chlorine gas was bubbled through the solution at 10° to 15° C. for 3 hours. The reaction mixture was then stirred at room temperature for 30 minutes, after which it was diluted with 500 ml of water and extracted with dichloromethane. The extract was washed with water and dried (MgSO$_4$) and the solvent was distilled off. The residue was dissolved in dichloromethane (250 ml) and ammonia gas was bubbled through the solution at 10° to 15° C. for 2 hours. The insolubles were filtered off and the filtrate was washed with water and dried (MgSO$_4$). The solvent was then distilled off. The residue was subjected to silica gel column chromatography and elution was carried out with hexane-ethyl acetate (3:1) to provide 40.7 g of the title compound as colorless oil.

NMR (CDCl$_3$) δ: 1.23 (6H, s), 1.26 (3H, t, J=7.2 Hz), 2.00–2.13 (2H, m), 3.06–3.19 (2H, m), 4.14 (2H, q, J=7.2 Hz), 4.86 (2H, br)

REFERENCE EXAMPLE 4

Production of 4-hydroxy-3,3-dimethyl-1-butanesulfonamide

While a suspension of 0.35 g of lithium aluminum hydride in 30 ml of tetrahydrofuran was stirred with ice-cooling, a solution of 1.5 g of ethyl 4-aminosulfonyl-2,2-dimethylbutyrate in 8 ml of tetrahydrofuran was added dropwise. After completion of dropwise addition, the mixture was stirred at 0° C. for 30 minutes and, then, at room temperature for 30 minutes. To this reaction mixture was added aqueous tetrahydrofuran for decomposition of excess lithium aluminum hydride and the mixture was neutralized with 2N-hydrochloric acid and extracted with ethyl acetate. The extract was washed with water and dried (MgSO$_4$) and the solvent was distilled off. The residue was subjected to silica gel column chromatography and elution was carried out with hexane-ethyl acetate (1:1) to provide 0.94 g of the title compound. m.p.: 75°–76° C.

Elemental analysis: for C$_6$H$_{15}$NO$_3$S Calcd. (%): C, 39.75; H, 8.34; N, 7.73 Found (%): C, 39.80; H, 8.10; N, 7.92

REFERENCE EXAMPLE 5

Production of 4-(N,N-dimethylaminomethylene)amino-sulfonyl-2,2-dimethyl-1-butanol To a suspension of 2.3 g of 4-hydroxy-3,3-dimethyl-1-butanesulfonamide in 40 ml of toluene was added 1.59 g of N,N-dimethylformamide dimethyl acetal and the mixture was stirred at 70° C. for 40 minutes. The solvent was then distilled off and the residue was recrystallized from ethyl ether to provide 2.86 g of the title compound.

NMR (CDCl$_3$) δ: 0.91 (6H, s), 1.69–1.84 (2H, m), 1.94 (1H, t, J=4.8 Hz), 2.98–3.11 (2H, m), 3.05 (3H, s), 3.14 (3H, s), 3.34 (2H, d, J=4.8 Hz), 8.05 (1H, s)

REFERENCE EXAMPLE 6

Production of 3-(N,N-dimethylaminomethylene)amino-sulfonyl-2,2-diethyl-1-propanol A mixture of 6.0 g of 3-hydroxy-2,2-diethyl-1-propanesulfonamide, 4.0 g of N,N-3-dimethylformamide dimethyl acetal and 60 ml of toluene was stirred at 100° C. for 30 minutes. The solvent was then distilled off. The residue was subjected to silica gel column chromatography and elution was carried out with ethyl acetate-chloroform-methanol (20:20:1) to provide 6.4 g of the title compound as colorless oil.

NMR (CDCl$_3$) δ: 0.84 (6H, t, J=7.4 Hz), 1.49 (4H, q, J=7.4 Hz), 3.05 (4H, s), 3.15 (3H, s), 3.64 (2H, s), 8.05 (1H, s)

REFERENCE EXAMPLE 7

Production of 3-(N,N-dimethylaminomethylene)amino-sulfonyl-2,2-pentamethylene-1-propanol Using 3-hydroxy-2,2-pentamethylene-1-propanesulfonamide and N,N-dimethylformamide dimethyl acetal, the same reaction as in Reference Example 5 was conducted to produce the title compound.

NMR (CDCl$_3$) δ: 1.36–1.73 (10H, m), 2.72 (1H, br), 3.05 (3H, s), 3.14 (2H, s), 3.15 (3H, s), 3.72 (3H, s), 8.05 (1H, s)

REFERENCE EXAMPLE 8

Production of 4-(N,N-dimethylaminomethylene)amino-sulfonyl-1-iodo-2,2-dimethylbutane A mixture of 5.5 g of 4-hydroxy-3,3-dimethyl-1-butanesulfonamide, 3.98 g of N,N-dimethylformamide dimethyl acetal and 50 ml of benzene was stirred at 80° C. for 1 hour. The solvent was then distilled off and the residue was dissolved in 50 ml of dichloromethane. While this solution was stirred with ice-cooling, 6.6 ml of anhydrous trifluoromethanesulfonic acid was added dropwise. After completion of dropwise addition, the mixture was stirred for 20 minutes, at the end of which time 4.7 ml of 2,6-lutidine was added and the reaction was further conducted at 0° C. for 20 minutes. The reaction mixture was diluted with 100 ml of water and extracted with ethyl acetate. The extract was washed serially with aqueous solution of potassium hydrogen sulfate and water and dried and the solvent was distilled off. The resulting oil was dissolved in 100 ml of acetone and after 13.5 g of sodium iodide was added, the mixture was refluxed with stirring for 2 hours. After cooling, the reaction mixture was diluted with water and extracted with ethyl acetate. The extract was washed with water and dried and the solvent was distilled off. The residue was subjected to silica gel column chromatography and elution was carried out with ethyl acetate-hexane (3:1). The fractions containing the objective product were pooled and concentrated and the residue was crystallized from isopropyl ether to provide 8.44 g of the title compound. m.p. 81°–82° C.

Elemental analysis: for C$_9$H$_{19}$IN$_2$O$_2$S Calcd. (%): C, 31.22; H, 5.53; N, 8.09 Found (%): C, 31.67; H, 5.68; N, 8.18

NMR (CDCl$_3$) δ: 1.07 (6H, s), 1.78–1.91 (2H, m), 2.92–3.04 (2H, m), 3.06 (3H, s), 3.12 (2H, s), 3.16 (3H, s), 8.05 (1H, s)

REFERENCE EXAMPLE 9

Production of 1-cyano-4-(N,N-dimethylaminomethylene)aminosulfonyl-2,2-dimethylbutane A mixture of 1.85 g of 4-(N,N-dimethylaminomethylene)aminosulfonyl-1-iodo-2,2-dimethylbutane, 0.49 g of potassium cyanide, 0.06 g of 18-crown-6 and 30 ml of dimethyl sulfoxide was stirred at 100° C. for 14 hours. After cooling, the reaction mixture was diluted with 100 ml of water and extracted with ethyl acetate. The extract was washed with water and dried (MgSO$_4$) and the solvent was distilled off. The residue was subjected to silica gel (70 g) column chromatography and elution was carried out with ethyl acetate-hexane (9:1). The fractions containing the objective compound were pooled and concentrated and the residue was recrystallized from ethyl ether to provide 1.11 g of the title compound. m.p. 53°–54° C.

Elemental analysis for C$_{10}$H$_{19}$N$_3$O$_2$S Calcd. (%): C, 48.96; H, 7.81; N, 17.13 Found (%): C, 48.88; H, 7.82; N, 16.77

NMR (CDCl$_3$) δ: 1.10 (6H, s), 1.82–1.94 (2H, m), 2.27 (2H, s), 2.96–3.07 (2H, m), 3.05 (3H, s), 3.15 (3H, s), 8.04 (1H, s)

REFERENCE EXAMPLE 10

Production of methyl 5-aminosulfonyl-3,3-dimethylvalerate

A mixture of 0.49 g of the cyano compound obtained in Reference Example 9 and 10 ml of concentrated hydrochloric acid was stirred at 120° to 130° C. for 16 hours and, then, concentrated to dryness under reduced pressure. The residue was dissolved in 12 ml of methanol and after 4 drops of concentrated sulfuric acid was added, the mixture was refluxed for 14 hours. The methanol was distilled off and the residue was diluted with water and extracted with ethyl acetate. The extract was washed with water and dried (MgSO$_4$) and the solvent was distilled off. The residue was subjected to silica gel (60 g) column chromatography and elution was carried out with ethyl acetate-hexane (4:1) to provide 0.35 g of the title compound as oil.

NMR (CDCl$_3$) δ: 1.05 (6H, s), 1.84–1.98 (2H, m), 2.25 (2H, s), 3.10–3.23 (2H, m), 3.68 (3H, s), 5.01 (2H, bs)

REFERENCE EXAMPLE 11

Production of 5-(N,N-dimethylaminomethylene)aminosulfonyl-3,3-dimethyl-1-pentanol In 10 ml of tetrahydrofuran was dissolved 0.352 g of the methyl ester obtained in Reference Example 10 and while the solution was stirred with ice-cooling, a suspension of 0.101 g of lithium aluminum hydride in 20 ml of tetrahydrofuran was added dropwise. The mixture was further stirred at the same temperature for 40 minutes, after which aqueous tetrahydrofuran was added. The mixture was then neutralized with 2N-hydrochloric acid and extracted with ethyl acetate. The extract was washed with water and dried (MgSO$_4$) and the solvent was distilled off. The residue was dissolved in 8 ml of toluene followed by addition of 0.24 g of N,N-dimethylformamide dimethyl acetal. The mixture was stirred at 80° C. for 45 minutes, after which the solvent was distilled off. The residue was subjected to silica gel (60 g) column chromatography and elution was carried out with chloroform-methanol (20:1) to provide 0.286 g of the title compound as oil.

Elemental analysis: for C$_{10}$H$_{22}$N$_2$O$_3$S Calcd. (%): C, 47.97; H, 8.86; N, 11.19 Found (%): C, 47.71; H, 8.62; N, 11.44

NMR (CDCl$_3$) δ: 0.94 (6H, s), 1.52 (2H, t, J=7.2 Hz), 1.67–1.81 (3H, m), 2.94–3.06 (2H, m), 3.04 (3H, s), 3.14 (3H, s), 3.70 (2H, t, J=7.2 Hz), 8.03 (1H, s)

REFERENCE EXAMPLE 12

Production of 5-(N,N-dimethylaminomethylene)aminosulfonyl-1-iodo-3,3-dimethylpentane In 10 ml of dichloromethane was dissolved 0.25 g of the 5-(N,N-dimethylaminomethylene)aminosulfonyl-3,3-dimethyl-1-pentanol obtained in Reference Example 11 and while the solution was stirred with ice-cooling, 0.24 ml of anhydrous trifluoromethanesulfonic acid was added dropwise. After completion of dropwise addition, the mixture was stirred at the same temperature for 20 minutes. Then, 0.18 ml of 2,6-lutidine was added and the mixture was further stirred for 20 minutes. The reaction mixture was then diluted with water and extracted with dichloromethane. The extract was washed serially with aqueous solution of potassium hydrogen sulfate and water and dried (MgSO$_4$) and the solvent was distilled off. The residue was dissolved in 15 ml of acetone, followed by addition of 0.5 g of sodium iodide, and the mixture was refluxed for 2 hours. After cooling, the reaction mixture was diluted with water and extracted with ethyl acetate. The extract was washed with water and dried (MgSO$_4$) and the solvent was distilled off. The residue was subjected to silica gel (50 g) column chromatography and elution was carried out with ethyl acetate-hexane (4:1) to provide 0.267 g of the title compound. m.p. 105°–106° C.

Elemental analysis for C$_{10}$H$_{21}$IN$_2$O$_2$S Calcd. (%): C, 33.34; H, 5.88; N, 7.78 Found (%): C, 33.57; H, 5.97; N, 8.09

REFERENCE EXAMPLE 13

Production of 1-cyano-5-(N,N-dimethylaminomethylene)aminosulfonyl-3,3-dimethylpentane A mixture of 7.2 g of the 5-(N,N-dimethylaminomethylene)aminosulfonyl-1-iodo-3,3-dimethylpentane obtained in Reference Example 12, 1.95 g of potassium cyanide, 0.26 g of 18-crown-6 and 100 ml of dimethyl sulfoxide was stirred at 90° C. for 5 hours. After cooling, the reaction mixture was diluted with 300 ml of water and extracted with ethyl acetate. The extract was washed with water and dried and the solvent was distilled off under reduced pressure. The residue was subjected to silica gel (100 g) column chromatography and elution was carried out with ethyl acetate-chloroform (5:1). The fractions containing the objective product were pooled and concentrated to provide 4.23 g of the title compound as colorless oil.

NMR (CDCl$_3$) δ: 0.94 (6H, s), 1.57–1.80 (4H, m), 2.32 (2H, t, J=7.6 Hz), 2.91–3.04 (2H, m), 3.05 (3H, s), 3.15 (3H, s), 8.05 (1H, s)

REFERENCE EXAMPLE 14

Production of methyl 6-aminosulfonyl-4,4-dimethylhexanoate

A mixture of 3.6 g of the 1-cyano-5-(N,N-dimethylamino-methylene)aminosulfonyl-3,3-dimethylpentane obtained in Reference Example 13 and 30 ml of concentrated hydrochloric acid was stirred at 120° to 130° C. for 10 hours, at the end of which time it was concentrated to dryness under reduced pressure. The residue was dissolved in 50 ml of methanol, followed by addition of 0.3 ml of concentrated sulfuric acid, and the mixture was refluxed for 6 hours. The methanol was then distilled off and the residue was diluted with water and extracted with ethyl acetate. The extract was washed with water and dried and the solvent was distilled off. The residue was subjected to silica gel (100 g) column chromatography and elution was carried out with ethyl acetate-hexane (2:1) to provide 2.95 g of the title compound as oil.

NMR (CDCl$_3$) δ: 0.93 (6H, s), 1.54–1.85 (4H, m), 2.30 (2H, t, J=8.0 Hz), 3.10 (2H, d, J=8.0 Hz), 3.68 (3H, s), 4.89 (2H, bs)

REFERENCE EXAMPLE 15

Production of 6-(N,N-dimethylaminomethylene)aminosulfonyl-4,4-dimethyl-1-hexanol In 20 ml of tetrahydrofuran was dissolved 3.3 g of the methyl 6-aminosulfonyl-4,4-dimethylhexanoate obtained in Reference Example 14 and while the solution was stirred with ice-cooling, a suspension of 0.79 g of lithium aluminum hydride in 100 ml of tetrahydrofuran was added dropwise. The mixture was stirred at the same temperature for 40 minutes, after which aqueous tetrahydrofuran was added. The mixture was then neutralized with 2N-hydrochloric acid and extracted with ethyl acetate. The extract was washed with water and dried and the solvent was distilled off. The residue was dissolved in 50 ml of toluene, followed by addition of 1.85 ml of N,N-dimethylformamide dimethyl acetal, and the mixture was stirred at 80° C. for 1 hour. The solvent was then distilled off. The residue was subjected to silica gel (80 g) column chromatography and elution was carried out with chloroform-methanol (20:1) to provide 3.15 g of the title compound as oil.

NMR (CDCl$_3$) δ: 0.90 (6H, s), 1.20–1.33 (2H, m), 1.46–1.78 (4H, m), 1.61 (1H, s), 2.98 (2H, t, J=6.4 Hz), 3.05 (3H, s), 3.14 (3H, s), 3.62 (2H, t, J=6.4 Hz), 8.04 (1H, s)

REFERENCE EXAMPLE 16

Production of ethyl 5-bromo-2,2-dimethylvalerate

To a solution of 28.7 ml of diisopropylamine in 150 ml of tetrahydrofuran was added 126 ml of 1.6M n-butyllithium-hexane with stirring at −5° to 0° C. and the mixture was further stirred for 30 minutes. This reaction mixture was cooled to −78° C. and 26.7 ml of ethyl isobutyrate was added dropwise. The mixture was stirred for 1 hour, after which 41.8 g of 1,3-dibromopropane was added dropwise. The reaction mixture was stirred at −78° C. for 1 hour and then at room temperature for 2 hours. The mixture was then poured in aqueous solution of ammonium chloride and extracted with ethyl acetate. The extract was washed with water and dried. The solvent was then distilled off and the residue was subjected to vacuum distillation to provide 40.3 g of the title compound as colorless oil. b.p. 76°–78° C./0.27 mmHg NMR (CDCl$_3$) δ: 1.19 (6H, s), 1.25 (3H, t, J=7.2 Hz), 1.31–1.60 (4H, m), 3.30–3.50 (2H, m), 4.12 (2H, q, J=7.2 Hz)

REFERENCE EXAMPLE 17

Production of ethyl 6-bromo-2,2-dimethylhexanoate

Using ethyl isobutyrate and 1,4-dibromobutane, the same reaction as in Reference Example 16 was conducted to produce the title compound. b.p. 62°–64° C./0.4 mmHg NMR (CDCl$_3$) δ: 1.17 (6H, s), 1.25 (3H, t, J=7.2 Hz), 1.33–1.63 (4H, m), 3.33–3.50 (4H, m), 4.12 (2H, q, J=7.2 Hz)

REFERENCE EXAMPLE 18

Production of ethyl 4-chloro-2,2-diethybutyrate

Using ethyl 2-ethylbutyrate and 1-bromo-2-chloroethane, the same reaction as in Reference Example 16 was conducted to produce the title compound. b.p. 69°–72° C./0.3 mmHg NMR (CDCl$_3$) δ: 0.81 (6H, t, J=7.1 Hz), 1.26 (3H, t, J=7.2 Hz), 1.61 (4H, q, J=7.2 Hz), 2.07 (2H, t, J=8.6 Hz), 3.45 (2H, t, J=8.6 Hz), 4.15 (2H, q, J=7.1 Hz)

REFERENCE EXAMPLE 19

Production of ethyl 5-bromo-2,2-diethylvalerate

Using ethyl 2-ethylbutyrate and 1,3-dibromopropane, the same reaction as in Reference Example 16 was conducted to produce the title compound. b.p. 98°–102° C./0.3 mmHg NMR (CDCl$_3$) δ: 0.79 (6H, t, J=7.4 Hz), 1.25 (3H, t, J=7.0 Hz), 1.51–1.86 (8H, m), 3.39 (2H, t, J=6.2 Hz), 4.14 (2H, q, J=7.0 Hz)

REFERENCE EXAMPLE 20

Production of ethyl 6-bromo-2,2-diethylhexanate

Using ethyl 2-ethylbutyrate and 1,4-dibromobutane, the same reaction as in Reference Example 16 was conducted to produce the title compound. b.p. 125°–130° C./0.3 mmHg NMR (CDCl$_3$) δ: 0.80 (6H, t, J=7.6 Hz), 1.27 (3H, t, J=7.0 Hz), 1.49–1.78 (4H, m), 1.61 (4H, q, J=7.6 Hz), 2.90–3.02 (2H, m), 4.15 (2H, q, J=7.0 Hz)

REFERENCE EXAMPLE 21

Production of ethyl 2,2-dimethyl-5-thiocyanovalerate

In 120 ml of dimethylformamide were dissolved 40.3 g of the ethyl 5-bromo-2,2-dimethylvalerate obtained in Reference Example 16 and 18.2 g of potassium thiocyanate and the mixture was stirred at 85° C. for 5 hours. The reaction mixture was then poured in 500 ml of water and extracted with ethyl ether and the extract was washed with water and dried. The solvent was distilled off and the residue was subjected to vacuum distillation to provide 35.7 g of the title compound as oil. b.p. 116°–118° C./0.3 mmHg

REFERENCE EXAMPLE 22

Production of ethyl 2,2-dimethyl-6-thiocyanohexanoate

Using the ethyl 6-bromo-2,2-dimethylhexanoate obtained in Reference Example 17 and potassium thiocyanate, the same reaction as in Reference Example 21 was conducted to product the title compound. b.p. 123°–125° C./0.4 mmHg NMR (CDCl$_3$) δ: 1.17 (6H, s), 1.25 (3H, t, J=7.2 Hz), 1.33–1.65 (4H, m), 1.73–2.08 (2H, m), 2.94 (2H, t, J=7.2 Hz), 4.12 (2H, q, J=7.2 Hz)

REFERENCE EXAMPLE 23

Production of ethyl 2,2-diethyl-4-thiocyanobutyrate

Using the ethyl 4-chloro-2,2-diethylbutyrate obtained in Reference Example 18 and potassium thiocyanate, the same reaction as in Reference Example 21 was conducted to product the title compound. b.p. 105°–108° C./0.3 mmHg NMR (CDCl$_3$) δ: 0.81 (3H, t, J=7.4 Hz), 0.83 (3H, t, J=7.4 Hz), 1.27 (3H, t, J=7.0 Hz), 1.54–1.72 (4H, m), 2.00–2.13 (2H, m), 2.80–2.92 (2H, m), 4.17 (2H, q, J=7.0 Hz)

REFERENCE EXAMPLE 24

Production of ethyl 2,2-diethyl-5-thiocyanovalerate

Using the ethyl 5-bromo-2,2-diethylvalerate obtained in Reference Example 19 and potassium thiocyanate, the same reaction as in Reference Example 21 was conducted to produce the title compound. b.p. 125°–130° C./0.3 mmHg NMR (CDCl$_3$) δ: 0.80 (6H, t, J=7.6 Hz), 1.27 (3H, t, J=7.0 Hz), 1.49–1.78 (4H, m), 1.61 (4H, q, J=7.6 Hz), 2.90–3.02 (2H, m), 4.15 (2H, q, J=7.0 Hz).

REFERENCE EXAMPLE 25

Production of ethyl 2,2-diethyl-6-thiocyanohexanoate

Using the ethyl 6-bromo-2,2-diethylhexanoate obtained in Reference Example 20 and potassium thiocyanate, the same reaction as in Reference Example 21 was conducted to produce the title compound. b.p. 145°–148° C./0.3 mmHg NMR (CDCl$_3$) δ: 0.78 (6H, t, J=7.6 Hz), 1.25 (3H, t, J=7.0 Hz), 1.21–1.68 (8H, m), 1.82 (2H, m), 2.95 (2H, t, J=7.4 Hz), 4.14 (2H, q, J=7.0 Hz)

REFERENCE EXAMPLE 26

Production of ethyl 5-aminosulfonyl-2,2-dimethylvalerate

In a mixture of 150 ml of acetic acid and 150 ml of water was dissolved 35.68 g of the ethyl 2,2-dimethyl-5-thiocyanovalerate obtained in Reference Example 21 and while the solution was vigorously stirred, chlorine gas was bubbled through the solution at 10° to 15° C. for 1.2 hours. The mixture was further stirred at 0° C. for 1 hour, at the end of which time it was extracted with dichloromethane. The extract was washed with water and dried and the solvent was distilled off. The residue was dissolved in 200 ml of dichloromethane and ammonia gas was bubbled through the solution at 0° C. for 40 minutes. The insolubles were filtered off and the filtrate was washed with water and dried. The solvent was then distilled off. The residue was subjected to silica gel (150 g) column chromatography and elution was carried out with ethyl acetate-hexane (1:1) to provide 30 g of the title compound.

NMR (CDCl$_3$) δ: 1.20 (6H, s), 1.26 (3H, t, J=7.4 Hz), 1.61–1.93 (4H, m), 3.11 (2H, t, J=7.0 Hz), 4.14 (2H, q, J=7.4 Hz), 4.88 (2H, bs)

REFERENCE EXAMPLE 27

Production of ethyl 6-aminosulfonyl-2,2-dimethylhexanoate

Using the ethyl 2,2-dimethyl-6-thiohexanoate obtained in Reference Example 22, the same reaction as in Reference Example 26 was conducted to produce the title compound.

NMR (CDCl$_3$) δ: 1.17 (6H, s), 1.25 (3H, t, J=7.2 Hz), 1.32–1.64 (4H, m), 1.85 (2H, t, J=7.6 Hz), 3.12 (2H, t, J=7.6 Hz), 4.12 (2H, q, J=7.2 Hz), 4.84 (2H, bs)

REFERENCE EXAMPLE 28

Production of ethyl 4-aminosulfonyl-2,2-dimethylbutyrate

Using the ethyl 2,2-diethyl-4-thiocyanobutyrate obtained in Reference Example 23, the same reaction as in Reference Example 26 was conducted to produce the title compound. m.p. 93°–94° C.

Elemental analysis: for C$_{10}$H$_{21}$NO$_4$S Calcd. (%): C, 47.79; H, 8.42; N, 5.57 Found (%): C, 47.73; H, 8.44; N, 5.70

NMR (CDCl$_3$) δ: 0.83 (6H, t, J=7.4 Hz), 1.27 (3H, t, J=7.0 Hz), 1.61 (4H, q, J=7.4 Hz), 2.03–2.16 (2H, m), 2.99–3.13 (2H, m), 4.17 (2H, q, J=7.0 Hz), 4.84 (2H, bs)

REFERENCE EXAMPLE 29

Production of ethyl 5-aminosulfonyl-2,2-diethylvalerate

Using the ethyl 2,2-diethyl-5-thiocyanovalerate obtained in Reference Example 24, the same reaction as in Reference Example 26 was conducted to produce the title compound. m.p. 66°–67° C.

Elemental analysis for C$_{11}$H$_{23}$NO$_4$S Calcd (%): C, 49.79, H, 8.74; N, 5.28 Found (%): C, 49.43; H, 8.81; N, 5.18

NMR (CDCl$_3$) δ: 0.79 (6H, t, J=7.4 Hz), 1.26 (3H, t, J=7.2 Hz), 1.61 (4H, q, J=7.4 Hz), 1.66–1.85 (4H, m), 3.11 (2H, t, J=6.6 Hz), 4.15 (2H, q, J=7.2 Hz), 4.84 (2H, bs)

REFERENCE EXAMPLE 30

Production of ethyl 6-aminosulfonyl-2,2-diethylhexanoate

Using the ethyl 2,2-diethylhexanoate obtained in Reference Example 25, the same reaction as in Reference Example 26 was conducted to produce the title compound.

NMR (CDCl$_3$) δ: 0.77 (6H, t, J=7.4 Hz), 1.25 (3H, t, J=7.2 Hz), 1.19–1.40 (2H, m), 1.58 (4H, q, J=7.4 Hz), 1.49–1.69 (2H, m), 1.85 (2H, m), 3.12 (2H, m), 4.13 (2H, q, J=7.2 Hz), 4.71 (2H, bs)

REFERENCE EXAMPLE 31

Production of 5-hydroxy-4,4-dimethyl-1-pentanesulfonamide

A solution of 7.1 g of the ethyl 5-aminosulfonyl-2,2-dimethylvalerate obtained in Reference Example 26 in 20 ml of tetrahydrofuran was added dropwise to a suspension of 1.71 g of lithium aluminum hydride in 100 ml of tetrahydrofuran with ice-cooling and stirring. After completion of dropwise addition, the mixture was stirred at 0° C. for 40 minutes and after addition of aqueous tetrahydrofuran for decomposition of excess lithium aluminum hydride, the mixture was neutralized with 2N-hydrochloric acid and extracted with ethyl acetate. The extract was washed with water and dried (MgSO$_4$) and the solvent was distilled off. The residue was subjected to silica gel (100 g) column chromatography and elution was carried out with hexane-ethyl acetate (4:1) to provide 3.39 g of the title compound as oil.

NMR (CDCl$_3$) δ: 0.90 (6H s), 1.35–1.50 (2H, m), 1.75–1.97 (2H, m), 3.12 (2H, t, J=7.8 Hz), 3.35 (2H, s), 5.04 (2H, bs)

REFERENCE EXAMPLE 32

Production of 6-hydroxy-5,5-dimethyl-1-hexanesulfonamide

Using the ethyl 6-aminosulfonyl-2,2-dimethylhexanoate obtained in Reference Example 27, the same reaction as in Reference Example 31 was conducted to produce the title compound.

NMR (CDCl$_3$) δ: 0.87 (6H, s), 1.21–1.54 (4H, m), 1.76–1.94 (2H, m), 2.05 (1H, s), 3.16 (2H, t, J=8 Hz), 3.31 (2H, s), 5.13 (2H, bs)

REFERENCE EXAMPLE 33

Production of 4-hydroxy-3,3-diethyl-1-butanesulfonamide

Using the ethyl 4-aminosulfonyl-2,2diethylbutyrate obtained in Reference Example 28, substantially the same reaction as in Reference Example 31 was conducted to produce the title compound. m.p. 79°–80° C.

Elemental analysis for C$_8$H$_{19}$NO$_3$S Calcd (%): C, 45.91; H, 9.15; N, 6.69 Found (%): C, 46.00; H, 9.20; N, 6.69

NMR (CDCl$_3$) δ: 0.74 (6H, t, J=7.4 Hz), 1.58 (4H, q, J=7.4 Hz), 1.50–1.66 (2H, m), 2.83–2.97 (2H, m), 3.11 (2H, s), 6.71 (2H, bs)

REFERENCE EXAMPLE 34

Production of 5-hydroxy-4,4-diethyl-1-pentanesulfonamide

Using the ethyl 5-aminosulfonyl-2,2diethylvalerate obtained in Reference Example 29, the same reaction as in Reference Example 31 was conducted to produce the title compound.

NMR (CDCl$_3$) δ: 0.79 (6H, t, J=7.6 Hz), 1.14–1.45 (6H, m), 1.70–1.89 (2H, m), 2.05 (1H, s), 3.12 (2H, t, J=7.6 Hz), 3.39 (2H, s), 5.18 (2H, bs)

REFERENCE EXAMPLE 35

Production of 6-hydroxy-5,5-diethyl-1-hexanesulfonamide

Using the ethyl 6-aminosulfonyl-2,2-diethylhexanoate obtained in Reference Example 30, the same reaction as in Reference Example 31 was conducted to produce the title compound. m.p. 64°–65° C.

Elemental analysis for C$_{10}$H$_{23}$NO$_3$S Calcd (%): C, 50.60, H, 9.77; N, 5.90 Found (%): C, 50.90; H, 9.58; N, 6.15

NMR (CDCl$_3$) δ: 0.78 (6H, t, J=7.2 Hz), 1.15–1.49 (4H, m), 1.23 (4H, q, J=7.2 Hz), 1.67 (1H, s), 1.85 (2H, m), 3.15 (2H, t, J=4.6 Hz), 3.35 (2H, s), 4.90 (2H, bs)

REFERENCE EXAMPLE 36

Production of 4-(N,N-dimethylaminomethylene)aminosulfonyl-2,2-diethyl-1-butanol

To a solution of 2.0 g of the 4-hydroxy-3,3-diethyl-1-butanesulfonamide obtained in Reference Example 33 in 30 ml of toluene was added 1.2 g of N,N-dimethylformamide dimethyl acetal and the mixture was stirred at 90° C. for 1 hour. The solvent was then distilled off under reduced pressure. The residue was subjected to silica gel (70 g) column chromatograhy and elution was carried out with ethyl acetate-chloroform-methanol (20:20:1) to provide 2.43 g of the title compound as oil.

NMR (CDCl$_3$) δ: 0.81 (6H, t, J=7.4 Hz), 1.15–1.38 (4H, m), 1.68–1.80 (2H, m), 1.96 (1H, bs), 2.96–3.07 (2H, m), 3.04 (3H, s), 3.14 (3H, s), 3.36 (2H, s), 8.05 (1H, s)

REFERENCE EXAMPLE 37

Production of 5-(N,N-dimethylaminomethylene)aminosulfonyl-2,2-diethyl-1-pentanol Using the 5-hydroxy-4,4-diethyl-1-pentanesulfonamide obtained in Reference Example 34, the same reaction as in Reference Example 36 was conducted to produce the title compound. m.p. 87°–88° C.

Elemental analysis for C$_{12}$H$_{26}$N$_2$O$_3$S Calcd (%): C, 51.77; H, 9.41; N, 10.06 Found (%): C, 51.75; H, 9.47; N, 10.09

NMR (CDCl$_3$) δ: 0.78 (6H, t, J=7.4 Hz), 1.18–1.41 (6H, m), 1.64 (1H, s), 1.70–1.85 (2H, m), 2.99 (2H, t, J=7.6 Hz), 3.04 (3H, s), 3.14 (3H, s), 3.37 (2H, s), 8.04 (1H, s)

REFERENCE EXAMPLE 38

Production of 2-isopropyl-1,3-propanediol

To a suspension of 4.17 g of lithium aluminum hydride in tetrahydrofuran was added 15 g of diethyl isopropyl malonate dropwise with ice-cooling and stirring. After completion of dropwise addition, the reaction mixture was stirred at 0° C. for 30 minutes and, then, at room temperature for 1 hour. To this mixture was added aqueous tetrahydrofurn for decomposing the excess reagent. The mixture was then neutralized with 6N-hydrochloric acid and the insolubles were filtered off. The filtrate was extracted with ethyl acetate and the extract was washed with water and dried (MgSO$_4$). The solvent was then distilled off under reduced pressure to provide 7.47 g of the title compound.

NMR (CDCl$_3$) δ: 0.92 (3H, s), 0.95 (3H, s), 1.49–1.65 (1H, m), 1.66–1.86 (1H, m), 2.32 (2H, bs), 3.72–3.93 (4H, m)

REFERENCE EXAMPLE 39

Production of 2-ethyl-2-methyl-1,3-propanediol

Using diethyl 2-ethyl-2-methylmalonate, the same reaction as in Reference Example 38 was conducted to produce the title compound. b.p. 78°–81° C./0.3 mmHg NMR (CDCl$_3$) δ: 0.81 (3H, s), 0.87 (3H, t, J=7.2 Hz), 1.38 (2H, q, J=7.2 Hz), 2.48 (2H, bs), 3.54 (4H, s)

REFERENCE EXAMPLE 40

Production of 3-bromo-2-isopropyl-1-propanol

In 150 ml of dichoromethane was dissolved 11.8 g of the 2-isopropyl-1,3-propanediol obtained in Reference Example 38, followed by addition of 26 g of triphenylphosphine. Then, with ice-cooling, 17.8 g of N-bromosuccinimide was added in small portions. This reaction mixture was stirred under ice-cooling for 30 minutes and, then, at room temperature for 1 hour. The reaction mixture was then concentrated under reduced pressure. The residue was subjected to silica gel (100 g) column chromatography and elution was carried out with ethyl acetate-hexane (3:7) to provide 11.87 g of the title compound as colorless oil.

NMR (CDCl$_3$) δ: 0.94 (3H, s), 0.98 (3H, s), 1.40–1.69 (2H, m), 1.71–1.93 (1H, m), 3.61–3.92 (4H, m)

REFERENCE EXAMPLE 41

Production of 3-bromo-2-ethyl-2-methyl-1-propanol

Using the 2-ethyl-2-methyl-1,3-propanediol obtained in Reference Example 39, the same reaction as in Reference Example 40 was conducted to produce the title compound.

NMR (CDCl$_3$) δ: 0.87 (3H, t, J=7.4 Hz), 0.96 (3H, s), 1.40 (2H, q, J=7.4 Hz), 1.53 (1H, bs), 3,40 (2H, s), 3.48 (2H, s)

REFERENCE EXAMPLE 42

Production of 3-acetoxy-2-isopropyl-1-propanethiocyanate

A mixture of 22 g of 3-bromo-2-isopropyl-1-propanol, 16.5 g of potassium thiocyanate and 100 ml of dimethylformamide was stirred at 100° C. for 15 hours. After cooling, 200 ml of diethyl ether and 200 ml of water were added to the reaction mixture and the organic layer was separated. The aqueous layer was extracted with 150 ml of diethyl acetate and the organic layers were combined, washed with saturated aqueous solution of sodium chloride and dried. The solvent was distilled off under reduced pressure. To the residue were added 17.4 g of acetic anhydride and 18.3 g of pyridine and the mixture was stirred at room temperature for 3 hours. The solvent was then distilled off under reduced pressure. The residue was subjected to silica gel (200 g) column chromatography and elution was carried out with ethyl acetate-hexane (1:5) to provide 14.07 g of the title compound as colorless oil.

NMR (CDCl$_3$) δ: 0.97 (3H, d, J=7.3 Hz), 1.01 (3H, d, J=7.3 Hz), 1.84–2.05 (2H, m), 2.08 (3H, s), 2.97–3.24 (2H, m), 4.03–4.35 (2H, m)

REFERENCE EXAMPLE 43

Production of 3-acetoxy-2-ethyl-2-methyl-1-propane thiocyanate

Using 3-bromo-2-ethyl-2-methyl-1-propanol, the procedure of Reference Example 42 was otherwise repeated to provide the title compound.

NMR (CDCl$_3$) δ: 0.90 (3H, t, J=7.4 Hz), 1.03 (3H, s), 1.46 (2H, q, J=7.4 Hz), 2.09 (3H, s), 3.07 (2H, s), 3.94 (2H, s)

REFERENCE EXAMPLE 44

Production of 3-acetoxy-2-isopropyl-1-propanesulfonamide

In a mixture of 50 ml of acetic acid and 50 ml of water was dissolved 10 g of 3-acetoxy-2-isopropyl-1-propane thiocyanate and while the solution was stirred vigorously, chlorine gas was bubbled through the solution at room temperature for 2 hours. The reaction mixture was extracted with dichloromethane and the extract was washed with saturated aqueous solution of sodium chloride and dried. The solvent was then distilled off under reduced pressure. The residue was dissolved in 100 ml of dichloromethane, and with cooling, ammonia gas was bubbled through the solution for 30 minutes, with the reaction temperature being controlled below 15° C. After the precipitate was filtered off, the filtrate was concentrated. The residue was subjected to silica gel (100 g) column chromatography and elution was carried out with methanol-chloroform (1:20) to provide 7.9 g of the title compound as oil.

NMR (CDCl$_3$) δ: 0.96 (3H, d, J=6.8 Hz), 0.98 (3H, d, J=6.8 Hz), 1.89–2.07 (1H, m), 2.08 (3H, s), 2.17–2.32 (1H, m), 3.11–3.19 (2H, m), 4.21–4.29 (2H, m), 4.87 (2H, bs)

REFERENCE EXAMPLE 45

Production of 3-acetoxy-2-ethyl-2-methyl-1-propanesulfonamide

Using 3-acetoxy-2-ethyl-2-methyl-1-propanethiocyanate, the same reaction as in Reference Example 44 was conducted to produce the title compound.

NMR (CDCl$_3$) δ: 0.90 (3H, t, J=7.4 Hz), 1.16 (3H, s), 1.57 (2H, q, J=7.4 Hz), 2.09 (3H, s), 3.24 (2H, dd, J=2.5 Hz & 4.9 Hz), 4.08 (2H, s), 4.86 (2H, bs)

REFERENCE EXAMPLE 46

Production of 3-hydroxy-2-isopropyl-1-propanesulfonamide

In 50 ml of methanol was dissolved 7.0 g of 3-acetoxy-2-isopropyl-1-propanesulfonamide and while the solution was stirred at room temperature, 6.5 g of 28 w/w % sodium methoxide was added and reacted for 30 minutes. The reaction mixture was then concentrated to dryness. The residue was subjected to silica gel (100 g) column chromatography and elution was carried out with chloroform-methanol (9:1) to provide 4.4 g of the title compound. m.p. 83°–84° C.

Elemental analysis for C$_6$H$_{15}$NO$_3$S Calcd (%): C, 39.67; H, 8.34; N, 7.73 Found (%): C, 39.72; H, 8.36; N, 7.78

NMR (d$_6$-DMSO) δ: 0.87 (3H, d, J=7.0 Hz), 0.87 (3H, d, J=7.0 Hz), 1.79–2.09 (2H, m), 2.85–2.95 (2H, m), 3.43–3.59 (2H, m), 4.55 (1H, bs), 6.77 (2H, bs)

REFERENCE EXAMPLE 47

Production of 3-hydroxy-2-ethyl-2-methyl-1-propanesulfonamide

Using 3-acetoxy-2-ethyl-2-methyl-1-propanesulfonamide, the same reaction as in Reference Example 46 was conducted to produce the title compound.

NMR (CDCl$_3$) δ: 0.90 (3H, t, J=7.4 Hz), 1.07 (3H, s), 1.33–1.68 (2H, m), 2.71 (1H, bs), 3.22 (2H, q, J=7.4 Hz), 3.61 (2H, s), 5.13 (2H, bs)

REFERENCE EXAMPLE 48

Production of ethyl 1-(2-chloroethyl)cyclohexanoate

Using ethyl cyclohexanoate, the same reaction as in Reference Example 1 was conducted to produce the title compound. b.p. 83°–86° C./0.25 mmHg NMR (CDCl$_3$) δ: 1.11–1.68 (8H, m), 1.27 (3H, t, J=7.2 Hz), 2.01 (2H, t, J=6.7 Hz), 1.91–2.16 (2H, m), 3.45 (2H, t, J=6.7 Hz), 4.16 (2H, q, J=7.2 Hz)

REFERENCE EXAMPLE 49

Production of ethyl 1-(2thiocyanoethyl)cyclohexnoate

Using ethyl 1-(2-chloroethyl)cyclohexonate, the same reaction as in Reference Example 2 was conducted to produce the title compound. b.p. 118°–122° C./0.25 mmHg NMR (CDCl$_3$) δ: 1.29 (3H, t, J=7.2 Hz), 1.14–1.66 (8H, m), 1.92–2.14 (4H, m), 2.80–2.90 (2H, m), 4.19 (2H, q, J=7.2 Hz)

REFERENCE EXAMPLE 50

Production of ethyl 1-(2-aminosulfonylethyl)cyclohexanoate

Using ethyl 1-(2-thiocyanoethyl)cyclohexanoate, the same reaction as in Reference Example 3 was conducted to produce the title compound.

NMR (CDCl$_3$) δ: 1.27 (3H, t, J=7.0 Hz), 1.16–1.71 (10 H, m), 1.94–2.14 (2H, m), 2.98–3.13 (2H, m), 4.17 (2H, q, J=7.0 Hz), 4.69 (2H, bs)

REFERENCE EXAMPLE 51

Production of 4-hydroxy-3,3-pentamethylene-1-butanesulfonamide

Using ethyl 1-(2-aminosulfonylethyl)cyclohexanoate, the same reaction as in Reference Example 4 was conducted to produce the title compound.

NMR (CDCl$_3$) δ: 1.19–1.56 (10H, m), 1.82–1.97 (2H, m), 2.05 (1H, s), 3.06–3.22 (2H, m), 3.43 (2H, s), 5.27 (2H, bs)

REFERENCE EXAMPLE 52

Production of 3-(N,N-dimethylaminomethylene)aminosulfonyl-2-isopropyl-1-propanol Using 3-hydroxy-2-isopropyl-1-propanesulfonamide, the same reaction as in Reference Example 5 was conducted to produce the title compound.

NMR (CDCl$_3$) δ: 0.91 (3H, d, J=6.6 Hz), 0.94 (3H, d, J=6.6 Hz), 1.64 (1H, bs), 1.82–2.11 (2H, m), 3.04 (3H, s), 3.11 (2H, d, J=6.6 Hz), 3.15 (3H, s), 3.63–3.93 (2H, m), 8.06 (1H, s)

REFERENCE EXAMPLE 53

Production of 3-(N,N-dimethylaminomethylene)aminosulfonyl-2-ethyl-2-methyl-1-propanol Using 3-hydroxy-2-ethyl-2-methyl-1-propanesulfonamide, the same reaction as in Reference Example 5 was conducted to produce the title compound.

NMR (CDCl$_3$) δ: 0.88 (3H, t, J=7.4 Hz), 1.05 (3H, s), 1.32–1.73 (2H, m), 3.04 (2H, q, J=7.4 Hz), 3.05 (3H, s), 3.15 (3H, s), 3.56–3.69 (2H, m), 8.05 (1H, s)

REFERENCE EXAMPLE 54

Production of 4-(N,N-dimethylaminomethylene)aminosulfonyl-2,2-pentamethylene-1-butanol Using 4-hydroxy-3,3-pentamethylene-1-butanesulfonamide, the same reaction as in Reference Example 5 was conducted to produce the title compound.

NMR (CDCl$_3$) δ: 1.22–1.54 (10H, m), 1.80–1.94 (4H, m), 3.05 (3H, s), 3.14 (3H, s), 3.41 (2H, s), 8.05 (1H, s)

REFERENCE EXAMPLE 55

Production of N,N-dimethyl-3-hydroxypropane-1-sulfonamide

Using 3-acetoxypropane-1-sulfonyl chloride and dimethylamine hydrochloride, the same reaction as in Reference Example 44 and 46 was conducted to produce the title compound.

NMR (CDCl$_3$) δ: 1.91 (1H, bS), 2.0–2.2 (2H, m), 2.89 (6H, s), 3.0–3.2 (2H, m), 3.7–3.9 (2H, m).

REFERENCE EXAMPLE 56

Production of 3-(1-methyl-4-piperazinylsulfonyl)-1-propanol

Using 3-acetoxypropane-1-sulfonyl chloride and 1-methylpiperazine, the same reaction as in Reference Example 44 and 46 was conducted to produce the title compound. m.p. 90°–93° C.

Elemental analysis for $C_8H_{18}N_2O_3S$ Calcd. (%): C, 43.22; H, 8.16; N, 12.60 Found. (%) : C, 43.01; H, 8.20; N, 12.53

FORMULATION EXAMPLE 1

(1) Compound of Example 1 10.0 mg
(2) Lactose 60.0 mg
(3) Corn starch 35.0 mg
(4) Gelatin 3.0 mg
(5) Magnesium stearate 2.0 mg Using 0.03 ml of a 10% aqueous solution of gelatin (3.0 mg as gelatin), a mixture of 10.0 mg of the compound of Example 1, 60.0 mg of lactose and 35.0 mg of corn starch was granulated by passage through a 1 mm-mesh sieve, dried at 40° C. and re-sieved. The resulting granules were blended with 2.0 mg of magnesium stearate and the blend was compression-molded. The resulting core tablet was sugar-coated with an aqueous suspension containing sucrose, titanium dioxide, talc and gum arabic. The thus-coated tablet was polished with beeswax to provide a coated tablet.

FORMULATION EXAMPLE 2

(1) Compound of Example 1 10.0 mg
(2) Lactose 70.0 mg
(3) Corn starch 50.0 mg
(4) Soluble starch 7.0 mg
(5) Magnesium stearate 3.0 mg Using 0.07 ml of an aqueous solution of soluble starch (7.0 mg as soluble starch), a mixture of the compound of Example 1 and 3.0 mg of magnesium stearate was granulated, dried and blended with 70.0 g of lactose and 50.0 mg of corn starch. The mixture was compression-molded to provide a tablet.

FORMULATION EXAMPLE 3

(1) Compound of Example 1 5.0 mg
(2) Sodium chloride 20.0 mg
(3) Distilled water 2 ml First, 5.0 mg of the compound obtained in Example 1 and 20.0 mg of sodium chloride were dissolved in distilled water and the solution was diluted with water to make 2.0 ml. The solution was filtered and aseptically filled into a 2 ml-ampul. The ampul was sterilized and sealed to provide an injectable solution.

EXPERIMENT

The results of a pharmacological test of the compound [I] or salt thereof according to the invention are shown below. [Effect on platelet activating factor (PAF)-induced guinea pig bronchoconstriction]

Male Hartley guinea pigs (body weights about 500 g) were used. Bronchoconstriction induced by PAF, 1 μg/kg i.v., in guinea pigs was measured using to the method of Konzett-Roessler. With the guinea pig immobilized in the dorsal position, tracheotomy was performed under urethane (1.5 g/kg i.v.) anesthesia and the trachea was connected through a cannula to a respirator. The side branch of the tracheal cannula was connected to a transducer (Model 7020, Ugobasile). With the volume of air per feed being controlled at 3–7 ml, the ventilation frequency at 70/min. and the pulmonary loading pressure at 10 cm $H_2O$, the volume of overflow air was recorded on a rectigraph (Recte-Hori-8s, San-ei Sokki) through the transducer. After administration of gallamine (1 mg/kg i.v.), PAF, 1 μg/kg, dissolved in physiological saline was administered through a jugular vein cannula and the induced bronchoconstriction was recorded for 15 minutes. The drug suspended in a 5% solution of gum arabic was administered orally in a dose of 30 mg/kg or 10 mg/kg one hour before PAF treatment. The results are presented in Table 1.

TABLE 1

Effect on PAF-induced bronchoconstriction in guinea pigs

| Example No. | % Inhibition of PAF-induced bronchoconstriction | |
|---|---|---|
| | 30 mg/kg, p.o. | 10 mg/kg, p.o. |
| 1 | 59 | — |
| 2 | 57 | — |
| 3 | 65 | 43 |
| 4 | — | 45 |
| 5 | — | 72 |
| 7 | — | 51 |
| 10 | — | 75 |
| 11 | — | 77 |
| 12 | — | 61 |

It will be apparent from Table 1 that the compound [I] or a salt thereof of the invention have excellent anti-PAF (platelet activating factor) activity. [Effect on leukotriene $C_4$ ($LTC_4$)-induced guinea pig bronchoconstriction]

Male Hartley guinea pigs (body weights about 500 g) were used. Bronchoconstriction induced by $LTC_4$, 20 μg/kg i.v., in guinea pigs was measured using to the method of Konzett-Rössler. With the guinea pig immobilized in the dorsal position, tracheotomy was performed under urethane (1.5 g/kg i.v.) anesthesia and the trachea was connected through a cannula to a respirator. The side branch of the tracheal cannula was connected to a transducer (Model 7020, Ugobasile). With the volume of air per feed being controlled at 3–7 ml, the ventilation frequency at 70/min. and the pulmonary loading pressure at 10 cm $H_2O$, the volume of overflow air was recorded on a rectigraph (Recte-Hori-8s, San-ei Sokki) through the transducer. After administration of gallamine (1 mg/kg i.v.), $LTC_4$, 20 μg/kg, dissolved in physiological saline was administered through a jagular vein cannula and the induced bronchoconstriction was recorded for 15 minutes. The drug suspended in a 5% solution of gum arabic was administered orally one hour before $LTC_4$ treatment. The results are presented in Table 2.

TABLE 2

Effect on $LTC_4$ - induced bronchoconstriction in guinea pigs.

| | Dose (mg/kg) | No. of animals | % Increase in respiratory airflow | % Inhibition |
|---|---|---|---|---|
| Control | — | 6 | 58.4 ± 1.1 | — |
| Example No. 5 | 1 | 6 | 43.9 ± 4.8* | 25 |
| | 3 | 6 | 26.7 ± 4.3** | 54 |
| | 10 | 6 | 18.9 ± 3.8** | 68 |

*P < 0.05,
**P < 0.01 vs control

It will be apparent from Table 2 that the compound [I] or a salt thereof of the invention have excellent anti-$LTC_4$ (leukotriene $C_4$) activity. [Effect on endothelin-1 (ET-1)-induced guinea pig bronchoconstriction]

Male Hartley guinea pugs (body weights about 500 g) were used. Bronchoconstriction induced by ET-1, 5 μg/kg i.v., in guinea pigs was measured using to the method of Konzett-Rössler. With the guinea pig immobilized in the dorsal position, tracheotomy was performed under urethane (1.5 g/kg i.v.) anesthesia and the trachea was connected through a cannula to a respirator. The side branch of the tracheal cannula was connected to a transducer (Model 7020, Ugobasile). With the volume of air per feed being controlled at 3–7 ml, the ventilation frequency at 70/min. and the pulmonary loading pressure at 10 cm $H_2O$, the volume of overflow air was recorded on a rectigraph (Recte-Hori-8s, San-ei Sokki) through the transducer. After administration of gallamine (1 mg/kg i.v.), ET-1, 5 μg/kg, dissolved in physiological saline was administered through a jagular vein cannula and the induced bronchoconstriction was recorded for 15 minutes. The drug suspended in a 5% solution of gum arbic was administrered orally one hour before ET-1 treatment. The results are presented in Table 3.

TABLE 3

Effect on endothelin-1 (ET-1)- induced bronchoconstriction in guinea pigs.

| | Dose (mg/kg) | No. of animals | % Increase in respiratory airflow | % Inhibition |
|---|---|---|---|---|
| Control | — | 6 | 49.5 ± 5.5 | — |
| Example No. 5 | 1 | 6 | 32.6 ± 7.4 | 34 |
| | 3 | 6 | 19.1 ± 3.8** | 61 |
| | 10 | 6 | 7.2 ± 1.0** | 86 |

**P < 0.01 vs control

It will be apparent from Table 3 that the compound [I] or a salt thereof of the invention have excellent anti-ET-1 (endothelin-1) activity.

What is claimed is:

1. A compound of the formula:

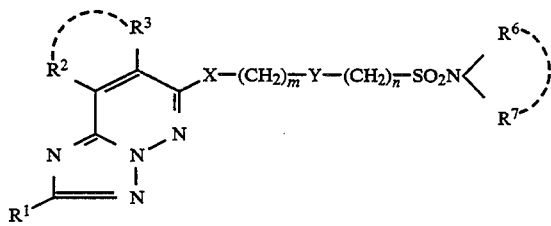

wherein $R^1$ stands for (i) a hydrogen atom, (ii) a $C_{1-6}$ alkyl group which may be substituted with one to four substituents selected from the group consisting of a hydroxy, amino, carboxyl, nitro, mono- or di-$C_{1-6}$ alkylamino, $C_{1-6}$ alkoxy, $C_{1-6}$ alkyl-carbonyloxy and halogen or (iii) a halogen atom;

$R^2$ and $R^3$ independently stand for stand for a hydrogen atom or a $C_{1-6}$ alkyl group which may be substituted with one to four substituents selected from the group consisting of a hydroxy, amino, carboxyl, nitro, mono- or di-$C_{1-6}$ alkylamino, $C_{1-6}$ alkoxy, $C_{1-6}$ alkyl-carbonyloxy and halogen;

X stands for an oxygen atom or $S(O)_p$, wherein p is a whole number of from 0 to 2;

Y stands for (i) a group of the formula:

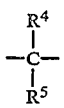

wherein $R^4$ and $R^5$ independently stand for a hydrogen atom or a $C_{1-6}$ alkyl group which may be substituted with one to four substituents selected from the group consisting of a hydroxy, amino, carboxyl, nitro, mono- or di-$C_{1-6}$ alkylamino, $C_{1-6}$ alkoxy, $C_{1-6}$ alkyl-carbonyloxy and halogen or (ii) a divalent homocyclic or heterocyclic ring selected from the group consisting of

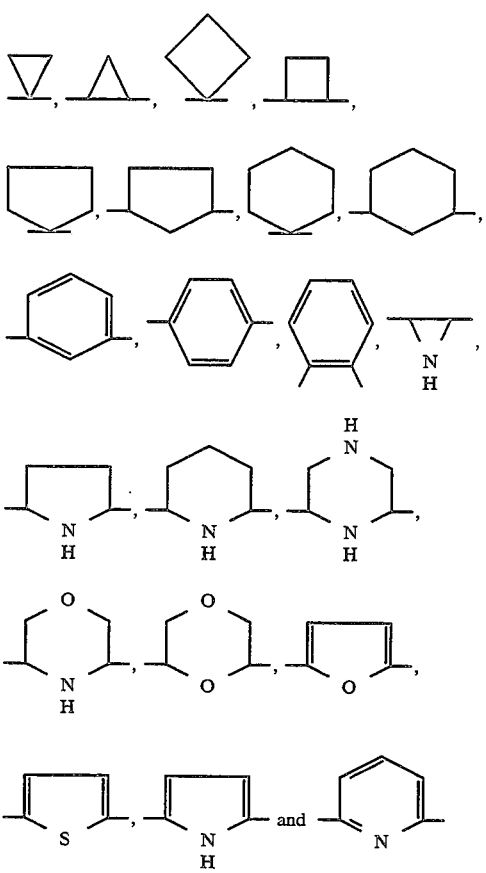

which may be substituted with 1 to 5 substituents selected from the group consisting of a $C_{1-6}$ alkyl group which may be substituted with 1 to 4 substituents selected from the group consisting of hydroxy, amino, mono- or di-$C_{1-6}$ alkylamino, $C_{1-6}$ alkoxy, $C_{1-6}$ alkyl-carbonyloxy and halogen, an amino group which may be substituted with 1 or 2 substituents selected from the group consisting of $C_{1-6}$ alkyl, $C_{1-6}$ acyl, pyrrolidino, morpholino, piperidino and piperazino, a hydroxy, a carboxyl, a nitro, a $C_{1-6}$ alkoxy, and a halogen;

$R^6$ and $R^7$ each stands for (i) a hydrogen, (ii) a $C_{1-6}$ alkyl group which may be substituted with one to four substituents selected from the group consisting of a hydroxy, amino, carboxyl, amino, carboxyl, nitro, mono- or di-$C_{1-6}$ alkylamino, $C_{1-6}$ alkoxy, $C_{1-6}$ alkyl-carbonyloxy and halogen, (iii) a $C_{3-6}$ cycloalkyl group which may be substituted with one to four substituents selected from the group consisting of a hydroxy, amino, carboxyl, nitro, mono- or di-$C_{1-6}$ alkylamino, $C_{1-6}$ alkoxy, $C_{1-6}$ alkyl-carbonyloxy and halogen, (iv) a $C_{6-14}$ aryl group which may be substituted with one to five substituents selected from the group consisting of a $C_{1-6}$ alkyl which may be substituted with one to four substituents selected from the group consisting of hydroxy, amino, mono- or di-$C_{1-6}$ alkylamino, $C_{1-6}$ alkoxy and halogen, an amino which can be substituted with one or two substituents selected from the group consisting of $C_{1-6}$ alkyl, pyrrolidino, morpholino, piperidino and piperazino, an acetamido, a hydroxy, a carboxyl, a nitro, a $C_{1-6}$ alkoxy, a $C_{1-6}$ alkylcarbonyloxy and a halogen, or (v) $R^6$ and $R^7$ taken together with the adjacent nitrogen atom form a nitrogen-containing heterocyclic ring selected from the group consisting of

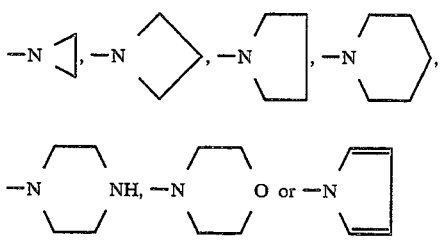

which may be substituted with 1 to 5 substituents selected from the group consisting of a $C_{1-6}$ alkyl group which may be substituted with 1 to 4 substituents selected from the group consisting of hydroxy, amino, mono- or di-$C_{1-6}$ alkylamino, $C_{1-6}$ alkoxy, $C_{1-6}$ alkylcarbonyloxy, and halogen, an amino group which may be substituted with 1 or 2 substituents selected from the group consisting of $C_{1-6}$ alkyl, $C_{1-6}$ acyl, pyrrolidino, morpholino, piperidino and piperazino, a hydroxy, a carboxyl, a nitro, a $C_{1-6}$ alkoxy and a halogen;

m stands for a whole number of from 0 to 4;

n stands for a whole number of from 0 to 4; or a pharmaceutically acceptable salt thereof.

2. A compound as claimed in claim 1, wherein the divalent group derived from a 3- to 7-membered homocyclic ring stands for a group of the formula:

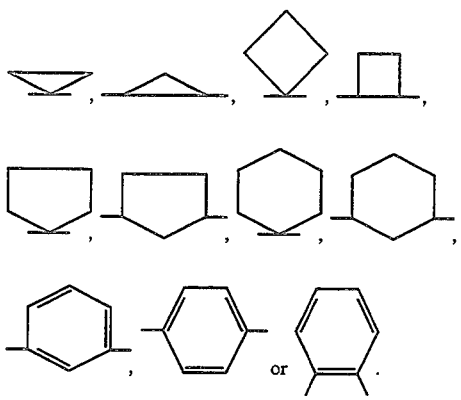

3. A compound as claimed in claim 1, wherein the divalent group derived from a 3- to 7-membered heterocyclic ring stands for a group of the formula:

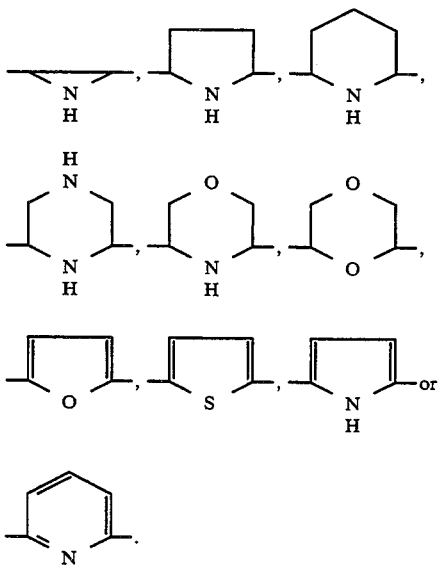

4. A compound as claimed in claim 1, wherein the nitrogen-containing heterocyclic group stands for a group of the formula:

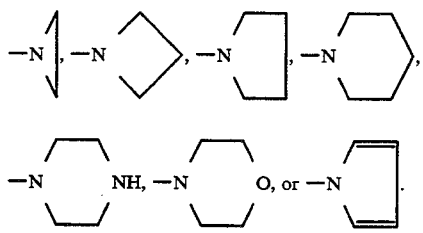

5. A compound as claimed in claim 1, wherein $R^1$ stands for a hydrogen atom or a $C_{1-3}$ alkyl group.

6. A compound as claimed in claim 1, wherein $R^2$ and $R^3$ independently stand for a hydrogen atom.

7. A compound as claimed in claim 1, wherein Y stands for (i) a group of the formula:

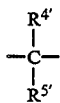

($R^{4'}$ and $R^{5'}$ independently stand for a hydrogen atom or a $C_{1-3}$ alkyl group which may be substituted with one to four substituents selected from the group consisting of a hydroxy, amino, carboxyl, nitro, mono- or di-$C_{1-6}$alkylamino, $C_{1-6}$ alkoxy, $C_{1-6}$ alkyl-carbonyloxy and halogen) or (ii) a group of the formula:

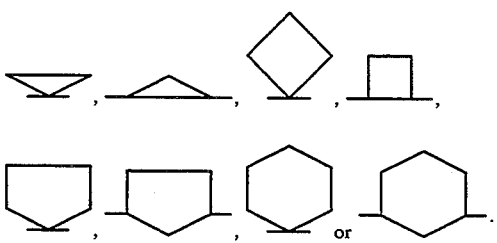

8. A compound as claimed in claim 1, wherein $R^6$ and $R^7$ respectively stand for a hydrogen atom or a $C_{1-3}$ alkyl group.

9. A compound as claimed in claim 1, wherein X stands for an oxygen atom.

10. A compound as claimed in claim 1, wherein $R^1$, $R^2$, and $R^3$ independently stand for a hydrogen atom or a $C_{1-3}$ alkyl group; Y stands for (i) a group of the formula:

($R^{4''}$ and $R^{5''}$ independently stand for a hydrogen atom or a $C_{1-3}$ alkyl group) or (ii) a group of the formula:

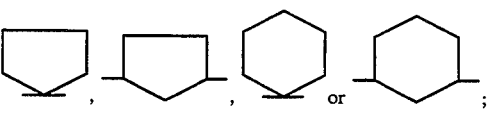

$R^6$ and $R^7$ independently stand for (i) a hydrogen atom or (ii) a $C_{1-3}$ alkyl group, or (iii) they can, taken together with the adjacent nitrogen atom, form a group of the formula:

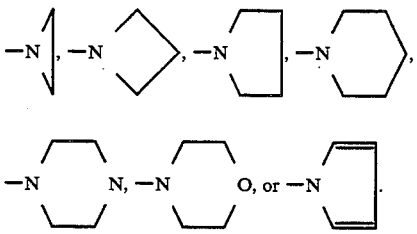

which is optionally substituted with 1 to 5 substituents selected from the group consisting of a $C_{1-6}$ alkyl group which can be substituted with 1 to 4 substituents selected from the group consisting of hydroxy, amino, mono- or di-$C_{1-6}$alkylamino, $C_{1-6}$ alkoxy, $C_{1-6}$ alkyl-carbonyloxy, and halogen, an amino group which can be substituted with 1 or 2 substituents selected from the group consisting of $C_{1-6}$ alkyl, $C_{1-6}$ acyl, pyrrolidino, morpholino, piperidino and piperazino, a hydroxy, a carboxyl, a nitro, a $C_{1-6}$ alkoxy and a halogen; X stands for an oxygen or sulfur atom; m stands for a whole number of 1 to 3; and n stands for a whole number of 1 to 4.

11. A compound as claimed in claim 1, wherein $R^1$, $R^2$ and $R^3$ independently stand for a hydrogen atom or a $C_{1-3}$ alkyl group; Y stands for (i) group of the formula:

($R^{4''}$ and $R^{5''}$ respectively stand for a hydrogen atom or a $C_{1-3}$ alkyl group) or (ii) a group of the formula:

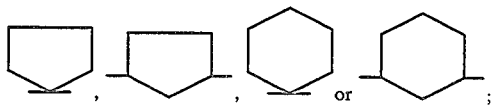

$R^6$ and $R^7$ respectively stand for a hydrogen atom or a $C_{1-3}$ alkyl group; X stands for an oxygen atom; m stands for a whole number of 1 to 3; and n stands for a whole number of 1 to 4.

12. A compound as claimed in claim 1, wherein $R^1$ and $R^2$ both are a hydrogen atom; $R^3$ is a $C_{1-3}$ alkyl group; Y stands for (i) a group of the formula:

($R^{4'''}$ and $R^{5'''}$ stand for a $C_{1-3}$ alkyl group) or (i) a group of the formula:

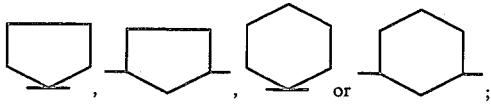

$R^6$ and $R^7$ both are a hydrogen atom; X stands for a oxygen atom; m is 1; and n is a whole number of 1 to 4.

13. A compound as claimed in claim 1, wherein $R^1$, $R^2$, $R^3$, $R^4$, $R^5$, $R^6$ and $R^7$ respectively stand for a hydrogen atom or a $C_{1-3}$ alkyl group; X stands for an oxygen atom; m is 1; and n is a whole number of 1 to 4.

14. A compound as claimed in claim 1, wherein $R^1$, $R^2$, $R^3$, $R^4$, and $R^5$ respectively stand for a hydrogen atom or a $C_{1-3}$ alkyl group; and

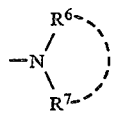

stands for a group of the formula:

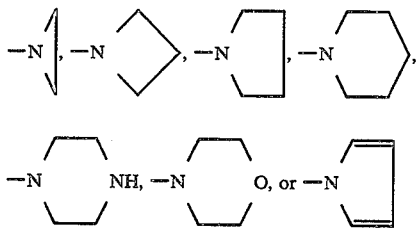

which may be substituted with one to five substituents selected from the group consisting of an optionally substituted $C_{1-6}$ alkyl, optionally substituted amino, hydroxy, carboxyl, nitro, $C_{1-6}$ alkoxy and halogen.

15. A compound as claimed in claim 1, wherein $R^1$, $R^2$, $R^3$, $R^6$ and $R^7$ stand for a hydrogen atom; $R^4$ and $R^5$ independently stand for a $C_{1-3}$ alkyl group; X stands for an oxygen atom; and m and n both are 1.

16. A compound as claimed in claim 1, which is 6-(2,2-diethyl-3-sulfamoyl-1-propoxy)-7-methyl[1,2,4]-triazolo[1,5-b]pyridazine.

17. A compound as claimed in claim 1, which is 6-(2,2-diethyl-6-sulfamoyl-1-hexyloxy)-7-methyl[1,2,4]-triazolo[1,5-b]pyridazine.

18. A compound as claimed in claim 1, which is 6-(2,2-diethyl-5-sulfamoyl-1-pentyloxy)-7-methyl[1,2,4]-triazolo[1,5-b]pyridazine.

19. A compound as claimed in claim 1, which is 6-(2,2-diethyl-4-sulfamoyl-1-butoxy)-7-methyl[1,2,4]-triazolo[1,5-b]pyridazine.

20. A compound of the formula:

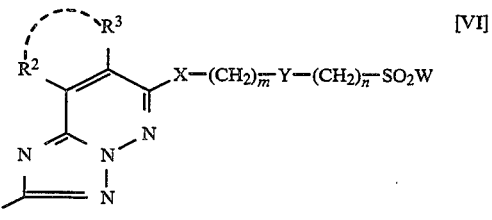

wherein W stands for a halogen, $C_{6-10}$ arylsulfonyloxy, or $C_{1-4}$ alkylsulfonyloxy;

$R^1$ stands for (i) a hydrogen atom, (ii) a $C_{1-6}$ alkyl group which may be substituted with one to four substituents selected from the group consisting of a hydroxy, amino, carboxyl, nitro, mono- or di-$C_{1-6}$ alkylamino, $C_{1-6}$ alkoxy, $C_{1-6}$ alkyl-carbonyloxy and halogen or (iii) a halogen atom;

$R^2$ and $R^3$ independently stand for stand for a hydrogen atom or a $C_{1-6}$ alkyl group which may be substituted with one to four substituents selected from the group consisting of a hydroxy, amino, carboxyl, nitro, mono- or di-$C_{1-6}$ alkylamino, $C_{1-6}$ alkoxy, $C_{1-6}$ alkyl-carbonyloxy and halogen;

X stands for an oxygen atom or $S(O)_p$, wherein p is a whole number of from 0 to 2;

Y stands for (i) a group of the formula:

wherein $R^4$ and $R^5$ independently stand for a hydrogen atom or a $C_{1-6}$ alkyl group which may be substituted with one to four substituents selected from the group consisting of a hydroxy, amino, carboxyl, nitro, mono- or di-$C_{1-6}$ alkylamino, $C_{1-6}$ alkoxy, $C_{1-6}$ alkyl-carbonyloxy and halogen or (ii) a divalent homocyclic or heterocyclic ring selected from the group consisting of

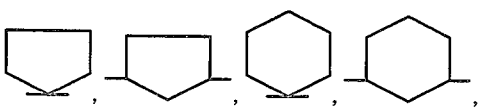

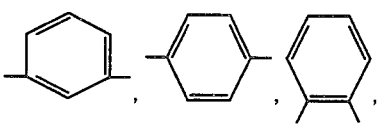

-continued

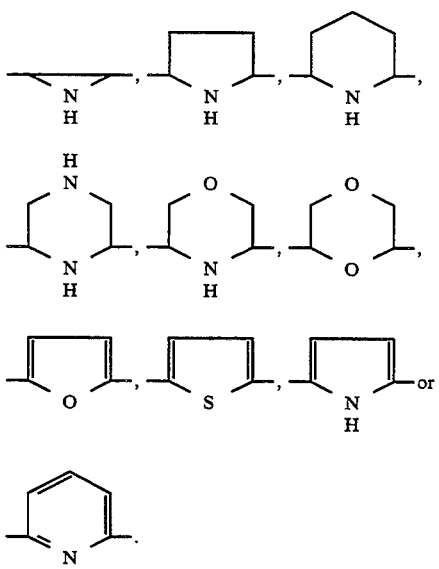

which may be substituted with 1 to 5 substituents selected from the group consisting of a $C_{1-6}$ alkyl group which may be substituted with 1 to 4 substituents selected from the group consisting of hydroxy, amino, mono- or di-$C_{1-6}$ alkylamino, $C_{1-6}$ alkoxy, $C_{1-6}$ alkyl-carbonyloxy and halogen, an amino group which may be substituted with 1 or 2 substituents selected from the group consisting of $C_{1-6}$ alkyl, $C_{1-6}$ acyl, pyrrolidino, morpholino, piperidino and piperazino, a hydroxy, a carboxyl, a nitro, a $C_{1-6}$ alkoxy, and a halogen;

m is a whole number from 0 to 4 and n is a whole number from 0 to 4, or a pharmaceutically acceptable salt thereof.

21. An anti-asthmatic composition, a bronchoconstriction inhibitor or an anti-allergenic composition which comprises an effective amount of a compound as defined in claim 1 and a physiologically acceptable carrier.

22. A method for treating asthma in mammals which comprises administrating to a subject suffering therefrom an effective amount of a compound as claimed in claim 1 with a physiologically acceptable carrier.

23. A method for suppressing bronchismus or bronchoconstriction in mammals which comprises administrating to a subject suffering therefrom an effective amount of a compound as claimed in claim 1 with a physiologically acceptable carrier.

* * * * *

UNITED STATES PATENT AND TRADEMARK OFFICE
CERTIFICATE OF CORRECTION

PATENT NO. : 5,389,633
DATED : February 14, 1995
INVENTOR(S) : MIYAKE et al.

It is certified that error appears in the above-indentified patent and that said Letters Patent is hereby corrected as shown below:

In the Abstract, line 23, "pharmasceutical" should read --pharmaceutical--.

Column 23,    line 59,    "amino-sulfonyl" should read --aminosulfonyl--.

Column 24,    line 7,    "amino-sulfonyl" should read --aminosulfonyl--;

line 24,    "amino-sulfonyl" should read --aminosulfonyl--;

line 36,    "amino-sulfonyl" should read --aminosulfonyl--.

Column 34,    line 60,    "2thiocyanoethyl" should read --2-thiocyanoethyl--.

UNITED STATES PATENT AND TRADEMARK OFFICE
CERTIFICATE OF CORRECTION

PATENT NO.   : 5,389,633
DATED        : February 14, 1995
INVENTOR(S)  : MIYAKE et al.

It is certified that error appears in the above-indentified patent and that said Letters Patent is hereby corrected as shown below:

Column 38, line 60, delete "stand for" (second occurrence).

Column 46, line 12, "An anti-asthmatic" should read --An anti-PAF, anti-asthmatic--.

Signed and Sealed this

Twenty-sixth Day of December, 1995

Attest:

BRUCE LEHMAN

*Attesting Officer*      *Commissioner of Patents and Trademarks*